(12) United States Patent
Donnelly et al.

(10) Patent No.: US 9,364,570 B2
(45) Date of Patent: Jun. 14, 2016

(54) FUNCTIONALISATION OF CAGE AMINE LIGANDS FOR METALLO-RADIOPHARMACEUTICALS

(71) Applicant: The University of Melbourne, Carlton (AU)

(72) Inventors: Paul Donnelly, Victoria (AU); Brett Paterson, Victoria (AU)

(73) Assignee: The University of Melbourne, Victoria (AU)

( * ) Notice: Subject to any disclaimer, the term of this patent is extended or adjusted under 35 U.S.C. 154(b) by 0 days.

(21) Appl. No.: 14/363,242

(22) PCT Filed: Dec. 6, 2012

(86) PCT No.: PCT/AU2012/001483
§ 371 (c)(1),
(2) Date: Jun. 5, 2014

(87) PCT Pub. No.: WO2013/082655
PCT Pub. Date: Jun. 13, 2013

(65) Prior Publication Data
US 2015/0051392 A1 Feb. 19, 2015

Related U.S. Application Data

(60) Provisional application No. 61/567,255, filed on Dec. 6, 2011.

(51) Int. Cl.
*A61K 51/04* (2006.01)
*C07D 487/08* (2006.01)
*A61K 51/08* (2006.01)
*A61K 47/48* (2006.01)

(52) U.S. Cl.
CPC ....... *A61K 51/0482* (2013.01); *A61K 47/48076* (2013.01); *A61K 51/082* (2013.01); *A61K 51/088* (2013.01); *C07D 487/08* (2013.01)

(58) Field of Classification Search
CPC .............. A61K 51/0482; A61K 47/48076; C07D 487/08
See application file for complete search history.

(56) References Cited

FOREIGN PATENT DOCUMENTS

WO WO-2010063069 A1 6/2010
WO WO-2013082655 A1 6/2013

OTHER PUBLICATIONS

Jarrett et al., Bioconjugate Chemistry (2000).*
"European Application Serial No. 12856248.5, Extended European Search Report mailed May 15, 2015", 6 pgs.
Bartolo, Nadine Di, et al., "New 64Cu PET imaging agents for personalised medicine and drug development using the hexa-aza cage, SarAr", Journal of Organic & Biomolecular Chemistry 17(4), (2006), 3350-3357.
Cooper, Maggie S, et al., "Comparison of 64Cu-Complexing Bifunctional Chelators for Radioimmunoconjugation: Labeling Efficiency, Specific Activity, and in Vitro/in Vivo Stability", Journal of Bioconjugate Chemistry 23(5), (2012), 1029-1039.
Voss, Stephan D, et al., "Positron emission tomography (PET) imaging of neuroblastoma and melanoma with 64Cu-SarAr immunoconjugates", Proceeding of the National Academy of Sciences of the United States of America 104(44), (Oct. 30, 2007), 17489-17493.
"International Application Serial No. PCT/AU2012/001483, International Preliminary Report on Patentability mailed Jun. 19, 2014", 8 pgs.
"International Application Serial No. PCT/AU2012/001483, International Search Report mailed Feb. 27, 2013", 3 pgs.
"International Application Serial No. PCT/AU2012/001483, Written Opinion mailed Feb. 27, 2013", 6 pgs.
Huang, Chiun-Wei, et al., "Biological Stability Evaluation of the alpha2β1 Receptor Imaging Agents: Diamsar and DOTA Conjugated DGEA Peptide", Bioconjugate Chemistry, 22(2), (2011), 256-263.
Jarrett, Benjamin R, et al., "Synthesis of 64Cu-Labeled Magnetic Nanoparticles for Multimodal Imaging", Bioconjugate Chemistry, 19, (2008), 1496-1504.
Ma, Michelle T, et al., "A new bifunctional chelator for copper radiopharmaceuticals: a cage amine ligand with a carboxylate functional group for conjugation to peptides", Chemical Communications, 22, (Apr. 23, 2009), 3237-3239.
Ma, Michelle T, et al., "Macrobicyclic Cage Amine Ligands for Copper Radiopharmaceuticals: A Single Bivalent Cage Amine Containing Two Lys3-bombesin Targeting Peptides", Inorganic Chemistry, 50, (2011), 6701-6710.
Wei, Lihui, et al., "64Cu-Labeled CB-TE2A and diamsar-conjugated RGD peptide analogs for targeting angiogenesis: comparison of their biological activity", Nuclear Medicine and Biology, 36, (2009), 277-285.

* cited by examiner

*Primary Examiner* — Paul V Ward
(74) *Attorney, Agent, or Firm* — Schwegman Lundberg & Woessner, P.A.

(57) ABSTRACT

The present invention relates to compounds that are useful as metal ligands and which contain a moiety capable of binding to a biological entity and methods of making these compounds. These compounds are of interest as they can be bound to a biological entity and then coordinated with a suitable metallic radionuclide. The coordinated compounds are useful as radiopharmaceuticals in the areas of radiotherapy and diagnostic imaging.

21 Claims, No Drawings

FUNCTIONALISATION OF CAGE AMINE LIGANDS FOR METALLO-RADIOPHARMACEUTICALS

PRIORITY APPLICATIONS

This application is a U.S. National Stage Filing under 35 U.S.C. 371 from International Application No. PCT/AU2012/001483, filed on 6 Dec. 2012, and published as WO 2013/082655 A1 on 13 Jun. 2013, which claims the benefit under 35 U.S.C. 119(e) to U.S. Provisional Application No. 61/567,255, filed on 6 Dec. 2011; which applications and publication are incorporated herein by reference in their entirety.

FIELD

The present invention relates to compounds that are useful as metal ligands and which contain a moiety capable of binding to a biological entity and methods of making these compounds. These compounds are of interest as they can be bound to a biological entity and then coordinated with a suitable metallic radionuclide. The coordinated compounds are useful as radiopharmaceuticals in the areas of radiotherapy and diagnostic imaging.

BACKGROUND

Radiolabelled compounds may be used as radiopharmaceuticals in a number of applications such as in radiotherapy or diagnostic imaging. In order for a radiolabelled compound to be employed as a radiopharmaceutical there are a number of desirable properties that the compound should ideally possess such as acceptable stability and, where possible, a degree of selectivity or targeting ability.

Initial work in the areas of radiopharmaceuticals focussed on simple metal ligands which were generally readily accessible and hence easy to produce. A difficulty with many of these radiolabelled compounds is that the complex formed between the ligand and the metal ion was not sufficiently strong and so dissociation of the metal ion from the ligand occurred in the physiological environment. This was undesirable as with the use of ligands of this type there was no ability to deliver the radiopharmaceutical to the desired target area in the body as metal exchange with metal ions in the physiological environment meant that when the radiopharmaceutical compound arrived at the desired site of action the level of radiolabelled metal ion coordinated to the compound had become significantly reduced. In addition where this type of exchange is observed the side effects experienced by the subject of the radiotherapy or radio-imaging are increased as radioactive material is delivered to otherwise healthy tissue in the body rather than predominantly to its place of action.

In order to overcome the problem of metal dissociation in the physiological environment a number of more complicated ligands have been developed and studied over time. Thus, for example a wide range of tetra-azamacrocycles based on the cyclam and cyclen framework have been investigated. Examples of ligands of this type include DOTA and TETA.

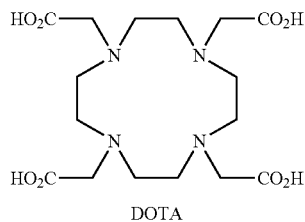

DOTA

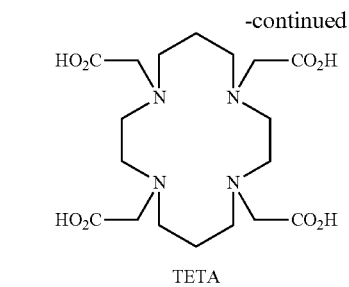

TETA

Unfortunately, even with these ligands there is still dissociation of the metal with certain derivatives. For example, some derivatives suffer from dissociation of Cu from the chelate as a consequence of transchelation to biological ligands such as copper transport proteins either as $Cu^{2+}$ or following in vivo reduction to $Cu^+$.

In order to increase the stability of radiolabelled compounds therefore hexaminemacrobicyclic cage amine ligands, known by their trivial name sarcophagines have been developed. These cage ligands form remarkably stable complexes with metals such as $Cu^{2+}$ and have fast complexation kinetics even at low concentrations of metal at ambient temperatures. These features therefore make ligands of this type particularly well suited in radiopharmaceutical applications, especially those applications involving copper.

Once the problem of stability of the complex between the ligand and the metal had been overcome attention turned to developing ways in which the ligand could be functionalised to incorporate targeting molecules within the ligand without compromising the stability of the metal ligand complex or the ultimate biological activity of the targeting molecule. A number of different targeting molecules are known in the art and the issue became how best to attach these to the ligand molecules.

In general the targeting molecule (or molecular recognition moiety as it is sometimes known) is attached to the ligand to provide a final compound containing both a ligand and a molecular recognition moiety. Whilst these compounds may contain a single molecular recognition moiety they may also be multimeric constructs where the ligand is attached to two (or more) molecular recognition moieties. This is typically desirable as a multimeric construct can possess higher affinity for a target receptor than its monomeric equivalent. This is in part due to an increase in the local concentration of the targeting group, allowing it to compete more effectively with endogenous ligands. In addition in circumstances where there is sufficient length between two or more targeting groups within a multimeric construct, then cooperative binding is possible, and two or more targeting groups will bind to two or more receptor sites at the same time. Indeed it has been observed that in vivo, a multimeric construct often demonstrates higher target tissue accumulation than its monomeric equivalent. Without wishing to be bound by theory it is thought that this is due to the higher affinity of the multimeric construct for the target receptor than that of the monomeric construct. Furthermore, the multimeric construct has a higher molecular weight than the monomeric construct and therefore prolonged bioavailability (as it is more resistant to degradation in the physiological environment). This can result in increased accumulation and retention in target tissue.

Initial work in the caged ligand area looked at direct coupling reactions of the primary amines of the cage amine 'diaminosarcophagine', 1,8-diamino-3,6,10,13,16,19-hexaaza bicyclo[6.6.6] icosane (($NH_2$)$_2$sar), with peptides using standard coupling procedures. Unfortunately for a variety of reasons this has proven to be relatively inefficient and work in this area ceased. Workers then focussed on the incorporation of an aromatic amine to produce SarAr. The pendent aromatic amine can be used in conjugation reactions with the carboxylate residues of peptides or antibodies and it has been shown that SarAr could be conjugated to anti-GD2 monoclonal antibody (14.G2a) and its chimeric derivative (ch14.8) and the conjugate has been radiolabelled with $^{64}$Cu.

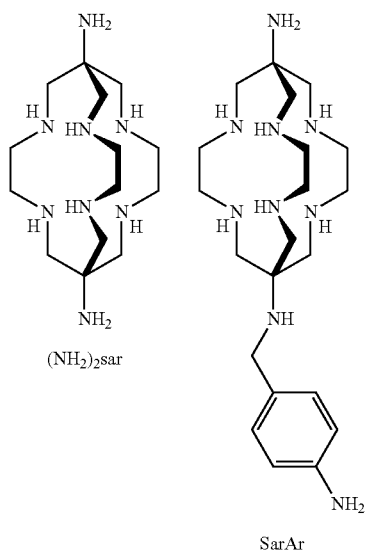

A difficulty with this approach is that in reaction of the aromatic amine in the conjugation step there are 8 other nitrogen atoms in the SarAr molecule that are available for competing reactions leading to the potential for the creation of a large number of impurities that is undesirable from a pharmaceutical sense. Whilst these could potentially be overcome by the use of substantial protective group chemistry this is clearly undesirable from a synthetic standpoint and scale up on a commercial scale.

An alternative approach has been to elaborate the ligand to incorporate carboxylate functional groups and incorporate peptides or antibodies via their N-terminal amine residues and this approach is of particular importance when the C-terminus is crucial to biological activity. Studies have shown that $(NH_2)_2$sar, can be functionalised with up to four carboxymethyl substituents via alkylation reactions with chloroacetic acid and the introduced carboxymethyl arms can be used as a point of further functionalisation and EDC-coupling reactions can then be used to introduce amino acids.

Unfortunately a potential disadvantage of these systems is that intramolecular cyclisation reactions can still occur in which the carboxymethyl arm reacts with a secondary amine of the cage framework to form lactam rings resulting in quadridentate rather than sexidentate ligands. Accordingly whilst this approach can be followed the potential for unwanted side reactions is clearly undesirable from a commercial perspective.

Further studies directed towards the functionalisation of $((NH_2)_2$sar) were based around its reaction with activated di-carbonyl compounds such as acid anhydrides leading to the formation of an amide bond to the amine nitrogen and a free carboxylic acid moiety which was available for further elaboration to the desired binding onto a molecular recognition moiety. A difficulty with this approach is that these reactions typically involve the use of coupling reagents which, given the intended end use of the compounds, may be undesirable especially if any residue is hard to remove. Accordingly there remains a need to develop new and improved methods of functionalising ligands of this type.

SUMMARY

In one aspect the present invention provides a method of attaching a moiety capable of binding to a biological entity to an amino substituted metal chelating ligand or a metal complex thereof the method comprising:
(a) reacting an amino substituted metal chelating ligand or a metal complex thereof with a molecule of the formula (1):

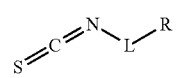

(1)

wherein L is a bond or a linking moiety and R is H or a moiety capable of binding to a biological entity or a protected form thereof or a synthon thereof; and
(b) isolating the compound or a metal complex thereof thus produced.

The step of reacting the amino substituted metal chelating ligand with the compound of formula (1) may be carried out on the ligand per se or a metal complex thereof. Whilst the reactions can be carried out on the uncomplexed ligand in many instances this is undesirable as nitrogen atoms in the nitrogen containing macrocyclic metal ligand may interfere with the desired reaction. As such by first forming the metal complex the metal acts to de-activate any nitrogens in the metal chelating ligand and so acts as a pseudo protecting group for these nitrogen atoms. As such in one embodiment it is desirable to carry out the reaction on the metal complex of the metal chelating ligand. A number of metals may be used for this purpose with magnesium being found to be particularly suitable.

By utilising the method above a large number of functionalised metal chelating ligands can be produced. Accordingly in an even further aspect the present invention provides a compound of the formula:

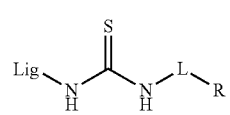

(2)

wherein L is a bond or a linking moiety;
R is H or a moiety capable of binding to a biological entity or a protected form thereof or a synthon thereof; and
Lig is a nitrogen containing macrocyclic metal ligand.

As with any group of structurally related compounds which possess a particular utility, certain embodiments of variables of the compounds of the formula (2) and are particularly useful in their end use application.

In the compounds of formula (1) and formula (2) the L moiety serves as a linking moiety that serves to act as a spacer between the nitrogen moiety and the moiety that is capable of binding to a biological entity. As such whilst it is desirable that there be a certain degree of separation between the two in order to ensure that the two entities do not interfere with each other's activity it is also important that the two are not so far removed such that the ligand (typically containing a radionuclide) is not effectively delivered to its site of operation.

In some embodiments L is a linking moiety having from 1 to 20 atoms in the normal chain. In some embodiments L is a linking moiety having from 1 to 15 atoms in the normal chain. In some embodiments L is a linking moiety having from 1 to 12 atoms in the normal chain. In some embodiments L is a linking moiety having from 1 to 10 atoms in the normal chain. In some embodiments L is a linking moiety having from 1 to 8 atoms in the normal chain. In some embodiments L has 8 atoms in the normal chain. In some embodiments L has 7 atoms in the normal chain. In some embodiments L has 6 atoms in the normal chain. In some embodiments L has 5 atoms in the normal chain. In some embodiments L has 4 atoms in the normal chain. In some embodiments L has 3 atoms in the normal chain. In some embodiments L has 2 atoms in the normal chain. In some embodiments L has 1 atom in the normal chain.

A wide range of possible moieties may be use to create a linking moiety of this type. Examples of suitable moieties that may be used in the creation of L include optionally substituted $C_1$-$C_{12}$alkyl, substituted $C_2$-$C_{12}$heteroalkyl, optionally substituted $C_3$-$C_{12}$cycloalkyl, optionally substituted $C_6$-$C_{18}$aryl, and optionally substituted $C_1$-$C_{18}$heteroaryl.

In some embodiments L is a group of the formula:

wherein each AA is independently an amino acid group;

q is an integer selected from the group consisting of 1, 2, 3, 4, 5, 6, 7, and 8;

r is an integer selected from the group consisting of 0, 1, 2, 3, 4, 5, 6, 7, and 8;

s is an integer selected from the group consisting of 0, 1, 2, 3, 4, 5, 6, 7, and 8.

In some embodiments q is 1. In some embodiments q is 2. In some embodiments q is 3. In some embodiments q is 4. In some embodiments q is 5. In some embodiments q is 6. In some embodiments q is 7. In some embodiments q is 8.

In some embodiments r is 0. In some embodiments r is 1. In some embodiments r is 2. In some embodiments r is 3. In some embodiments r is 4. In some embodiments r is 5. In some embodiments r is 6. In some embodiments r is 7. In some embodiments r is 8.

In some embodiments s is 0. In some embodiments s is 1. In some embodiments s is 2. In some embodiments s is 3. In some embodiments s is 4. In some embodiments s is 5. In some embodiments s is 6. In some embodiments s is 7. In some embodiments s is 8.

In some embodiments the amino acid is a naturally occurring amino acid. In some embodiments the amino acid is a non-naturally occurring amino acid. In some embodiments the amino acid is selected from the group consisting of phenyl alanine, tyrosine, amino hexanoic acid and cysteine.

In some embodiments q is 3, r is o and s is 5. In these embodiments X is a group of the formula:

In some embodiments L is a group of the formula:

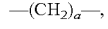

wherein optionally one or more of the $CH_2$ groups may be independently replaced by a heteroatomic group selected from S, O, P and $NR^4$ where $R^4$ is selected from the group consisting of H, optionally substituted $C_1$-$C_{12}$alkyl, optionally substituted $C_3$-$C_{12}$cycloalkyl, optionally substituted $C_6$-$C_{18}$aryl, and optionally substituted $C_1$-$C_{18}$heteroaryl;

a is an integer selected from the group consisting of 1, 2, 3, 4, 5, 6, 7, 8, 9, 10, 11, 12, 13, 14 and 15.

In some forms of these embodiments the L group may contain a poly ethoxy group (PEG). In some embodiments L is a group of the formula:

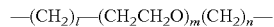

wherein l is an integer selected from the group consisting of 0, 1, 2, 3, 4, 5, 6, 7, 8, 9, and 10;

wherein m is an integer selected from the group consisting of 0, 1, 2, 3, 4, 5, 6, 7, 8, 9, and 10;

and wherein n is an integer selected from the group consisting of 0, 1, 2, 3, 4, 5, 6, 7, 8, 9, and 10.

In some embodiments l is selected from the group consisting of 0, 1, 2, 3, 4, and 5. In some embodiments l is 5. In some embodiments l is 4. In some embodiments l is 3. In some embodiments l is 2. In some embodiments l is 1. In some embodiments l is 0.

In some embodiments m is selected from the group consisting of 0, 1, 2, 3, 4, and 5. In some embodiments m is 5. In some embodiments m is 4. In some embodiments m is 3. In some embodiments m is 2. In some embodiments m is 1. In some embodiments m is 0.

In some embodiments n is selected from the group consisting of 0, 1, 2, 3, 4, and 5. In some embodiments n is 5. In some embodiments n is 4. In some embodiments n is 3. In some embodiments m is 2. In some embodiments n is 1. In some embodiments n is 0.

Specific examples of L groups of this type include —$CH_2$—($CH_2CH_2O$)$_3$($CH_2$)$_3$—; and —($CH_2CH_2O$)$_3$$CH_2$)$_2$—. As will be appreciated by a skilled worker in the field the values of I, m and n can be varied widely to arrive at a large number of possible L groups of this type.

In some embodiments L is a group of the formula:

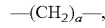

wherein optionally one or more of the $CH_2$ groups may be independently replaced by a heteroatomic group selected from S, O, P and $NR^4$ where $R^4$ is selected from the group consisting of H, optionally substituted $C_1$-$C_{12}$alkyl, optionally substituted $C_3$-$C_{12}$cycloalkyl, optionally substituted $C_6$-$C_{18}$aryl, and optionally substituted $C_1$-$C_{18}$heteroaryl; and a is an integer selected from the group consisting of 1, 2, 3, 4, 5, 6, 7, 8, 9 and 10.

In some embodiments a is selected from the group consisting of 1, 2, 3, 4, and 5. In some embodiments a is 4. In some embodiments a is 3. In some embodiments a is 2. In some embodiments a is 1.

In some embodiments L is selected from the group consisting of —$CH_2$—, —$CH_2CH_2$—, —$CH_2CH_2CH_2$—, —$CH_2CH_2CH_2CH_2$— and —$CH_2OCH_2$—.

In some embodiments L is —($CH_2$)—. In some embodiments L is —($CH_2$)$_2$—. In some embodiments L is —($CH_2$)$_3$—. In some embodiments L is —($CH_2$)$_4$—. In some embodiments L is —($CH_2$)$_5$—. In some embodiments L is —($CH_2$)$_6$—. In some embodiments L is —($CH_2$)$_7$—. In some embodiments L is —($CH_2$)$_8$—. In some embodiments L is —($CH_2$)$_9$—. In some embodiments L is —($CH_2$)$_{10}$—.

In the methods of the invention in theory any amino substituted metal chelating ligand may be used. In some embodiments the Lig used in the method of the invention may be a tetra-azamacrocycle based on the cyclam and cyclen framework.

In some embodiments the Lig is a nitrogen containing cage metal ligand. Cage ligands of this type are typically useful as they bind strongly to metal ions leading to a stable complex being formed.

In some embodiments the amino substituted metal chelating ligand used in the method of the invention is a compound of the formula Lig-NH$_2$. In these embodiments the ligand is reacted with one equivalent of the compound of formula (1) to produce a mono-functionalised ligand.

In some embodiments the amino substituted metal chelating ligand used in the method of the invention is a compound of the formula NH$_2$-Lig-NH$_2$. In these embodiments the ligand is reacted with two equivalents of the compound of formula (1) to produce a di-functionalised ligand.

In some embodiments the amino substituted metal chelating ligand used in the method of the invention is a compound of the formula NH$_2$-Lig-NH$_2$ and one of the nitrogen atoms is protected so that the other can be selectively functionalised. In these embodiments the ligand is reacted with one equivalent of the compound of formula (1) to produce a mono-functionalised ligand also containing a protected amine group. This protected amine group may be de-protected to produce the free mono-functionalised amine or it may be further functionalised so as to produce a differentially functionalised ligand where the functional group attached to each amine moiety of the original di-amine is different.

In some embodiments Lig used in the method of the invention is a nitrogen containing cage metal ligand of the formula:

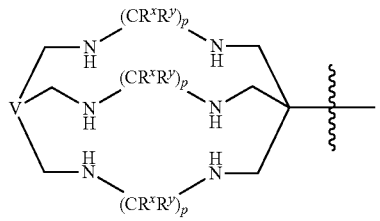

V is selected from the group consisting of N and CR$^1$;

each R$^x$ and R$_y$ are independently selected from the group consisting of H, CH$_3$, CO$_2$H, NO$_2$, CH$_2$OH, H$_2$PO$_4$, HSO$_3$, CN, CONH$_2$ and CHO;

each p is independently an integer selected from the group consisting of 2, 3, and 4;

R$^1$ is selected from the group consisting of H, OH, halogen, NO$_2$, NH$_2$, optionally substituted C$_1$-C$_{12}$alkyl, optionally substituted C$_6$-C$_{18}$aryl, cyano, CO$_2$R$^2$, NHR$^3$, N(R$^3$)$_2$;

R$^2$ is selected from the group consisting of H, halogen, an oxygen protecting group, optionally substituted C$_1$-C$_{12}$alkyl, optionally substituted C$_2$-C$_{12}$alkenyl, optionally substituted C$_2$-C$_{12}$alkynyl and optionally substituted C$_2$-C$_{12}$heteroalkyl;

each R$^3$ is independently selected from the group consisting of H, L-R', a nitrogen protecting group, optionally substituted C$_1$-C$_{12}$alkyl, —(C=O)-substituted C$_1$-C$_{12}$alkyl, optionally substituted C$_2$-C$_{12}$alkenyl, optionally substituted C$_2$-C$_{12}$alkynyl and optionally substituted C$_2$-C$_{12}$heteroalkyl.

wherein L is as defined above and R' is H, optionally substituted C$_1$-C$_{12}$alkyl, or a moiety capable of binding to a biological entity.

In some embodiments Lig used in the method of the invention is a macrocyclic metal ligand of the formula:

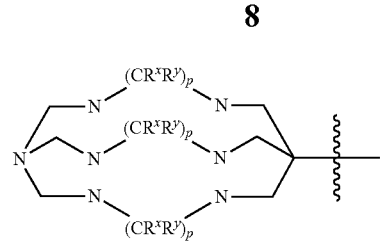

wherein R$^x$, R$^y$ and p are as defined above.

In some embodiments Lig is a macrocyclic ligand of the formula:

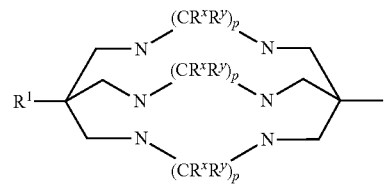

wherein R$^x$, R$^y$, R$^1$ and p are as defined above.

In some embodiments Lig is selected from the group consisting of:

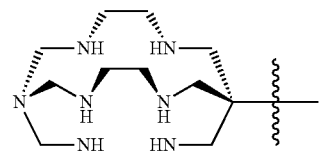

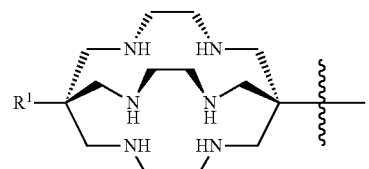

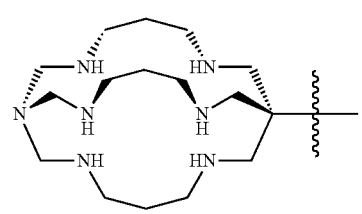

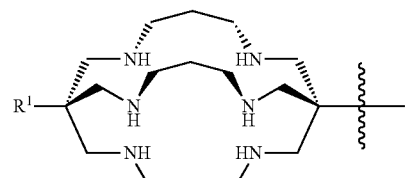

-continued

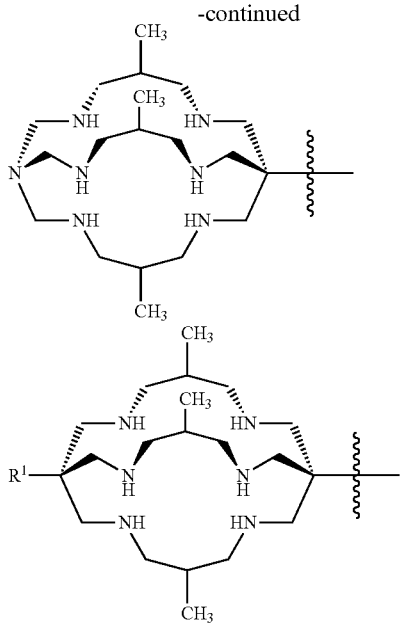

wherein R¹ is as defined above.
In some embodiments Lig is a group of the formula:

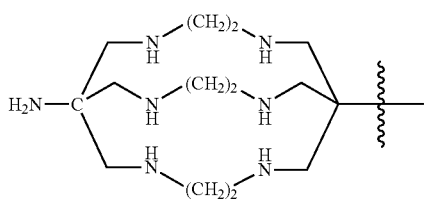

Specific examples of R¹ which may be present on the Lig group for use in the methods of the present invention include $NH_2$, methyl, ethyl, propyl, butyl, pentyl, hexyl, NHC(=O)$CH_3$, and —NHC(=O)$CH_2CH_2CH_2CO_2H$.

As discussed above the present invention provides a compound of the formula:

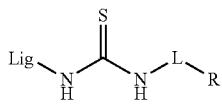

(2)

wherein L is a bond or a linking moiety;
R is a moiety capable of binding to a biological entity or a protected form thereof or a synthon thereof; and
Lig is a nitrogen containing macrocyclic metal ligand.

The nitrogen containing macrocyclic metal ligand (Lig) in the compounds of the invention may be any suitable macrocyclic ligand. In some embodiments Lig in the compounds of the invention may be a tetra-azamacrocycle based on the cyclam and cyclen framework. In some embodiments the Lig is a nitrogen containing cage metal ligand. Cage ligands of this type are typically useful as they bind strongly to metal ions leading to a stable complex being formed.

In some embodiments Lig in the compounds of the invention is a nitrogen containing cage metal ligand of the formula:

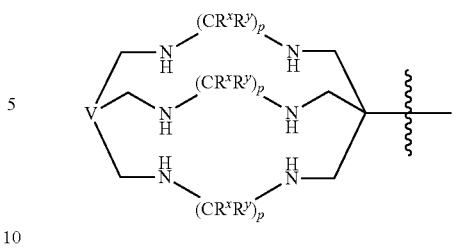

V is selected from the group consisting of N and $CR^1$;
each $R^x$ and $R^y$ are independently selected from the group consisting of H, $CH_3$, $CO_2H$, $NO_2$, $CH_2OH$, $H_2PO_4$, $HSO_3$, CN, $CONH_2$ and CHO;
each p is independently an integer selected from the group consisting of 2, 3, and 4;
$R^1$ is selected from the group consisting of H, OH, halogen, $NO_2$, $NH_2$, optionally substituted $C_1$-$C_{12}$alkyl, optionally substituted $C_6$-$C_{18}$aryl, cyano, $CO_2R^2$, $NHR^3$, $N(R^3)_2$ and a group of the formula:

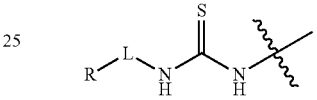

L is as defined above;
R is H or a moiety capable of binding to a biological entity or a protected form thereof or a synthon thereof;
$R^2$ is selected from the group consisting of H, halogen, an oxygen protecting group, optionally substituted $C_1$-$C_{12}$alkyl, optionally substituted $C_2$-$C_{12}$alkenyl, optionally substituted $C_2$-$C_{12}$alkynyl and optionally substituted $C_2$-$C_{12}$ heteroalkyl;
each $R^3$ is independently selected from the group consisting of H, L-R', a nitrogen protecting group, optionally substituted $C_1$-$C_{12}$alkyl, —(C=O)-substituted $C_1$-$C_{12}$alkyl, optionally substituted $C_2$-$C_{12}$alkenyl, optionally substituted $C_2$-$C_{12}$alkynyl and optionally substituted $C_2$-$C_{12}$ heteroalkyl.
wherein L is as defined above and R' is H, optionally substituted $C_1$-$C_{12}$alkyl, or a moiety capable of binding to a biological entity.

In some embodiments Lig in the compounds of the invention is a nitrogen containing cage metal ligand of the formula:

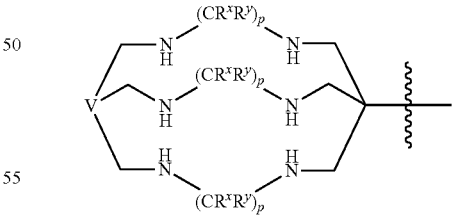

V is selected from the group consisting of N and $CR^1$;
each $R^x$ and $R^y$ are independently selected from the group consisting of H, $CH_3$, $CO_2H$, $NO_2$, $CH_2OH$, $H_2PO_4$, $HSO_3$, CN, $CONH_2$ and CHO;
each p is independently an integer selected from the group consisting of 2, 3, and 4;
$R^1$ is selected from the group consisting of H, OH, halogen, $NO_2$, $NH_2$, optionally substituted $C_1$-$C_{12}$alkyl, optionally substituted $C_6$-$C_{18}$aryl, cyano, $CO_2R^2$, $NHR^3$, $N(R^3)_2$;

$R^2$ is selected from the group consisting of H, halogen, an oxygen protecting group, optionally substituted $C_1$-$C_{12}$alkyl, optionally substituted $C_2$-$C_{12}$alkenyl, optionally substituted $C_2$-$C_{12}$alkynyl and optionally substituted $C_2$-$C_{12}$ heteroalkyl;

each $R^3$ is independently selected from the group consisting of H, a nitrogen protecting group, optionally substituted $C_1$-$C_{12}$alkyl, —(C=O)-substituted $C_1$-$C_{12}$alkyl, optionally substituted $C_2$-$C_{12}$alkenyl, optionally substituted $C_2$-$C_{12}$alkynyl and optionally substituted $C_2$-$C_{12}$ heteroalkyl.

In some embodiments Lig in the compounds of the invention is a macrocyclic metal ligand of the formula:

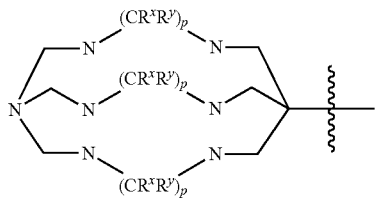

wherein $R^x$, $R^y$ and p are as defined above.

In some embodiments Lig in the compounds of the invention is a macrocyclic ligand of the formula:

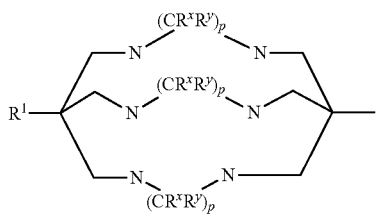

wherein $R^x$, $R^y$, $R^1$ and p are as defined above.

In some embodiments Lig in the compounds of the invention is selected from the group consisting of:

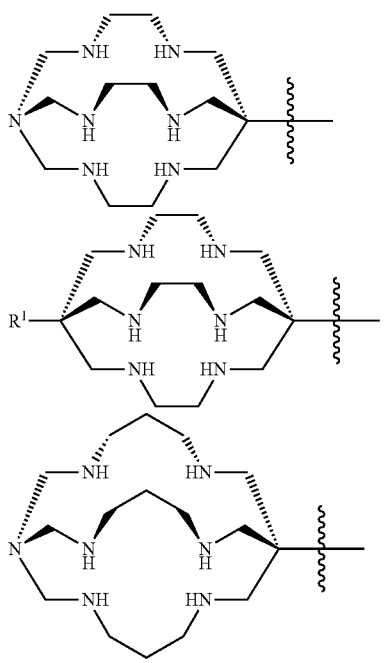

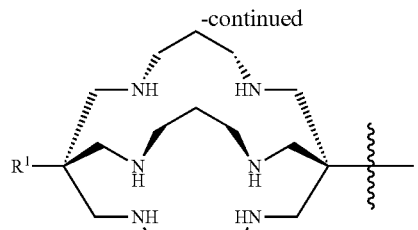

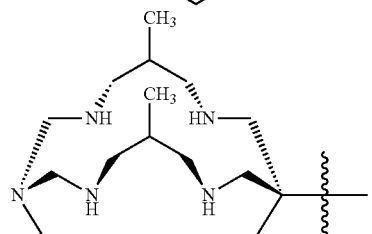

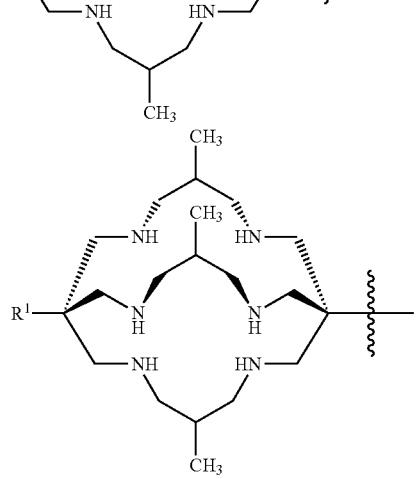

wherein $R^1$ is as defined above.

In some embodiments Lig in the compounds of the invention is a group of the formula:

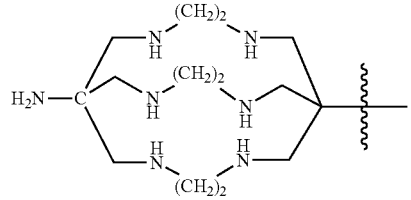

R is a moiety capable of binding to a biological entity, or a protected form thereof or a synthon thereof. The moiety may have the ability to bind to a biological moiety such as an antibody, a protein, a peptide, a carbohydrate, a nucleic acid, an oligonucleotide, an oligosaccharide and a liposome or a fragment or derivative thereof.

As such the R group reacts or binds to a complementary moiety on the biological entity of interest. For example in one embodiment the R moiety is a moiety capable of taking part in a click chemistry reaction with a complementary moiety on a biological entity. Examples of complementary paired functional groups that are well known to undergo "click" chemistry reactions are alkyne-azide, alkyne-nitrile oxide, nitrile-azide and maleimide-anthracene. Each of these paired complementary functional groups gives rise to cyclic moieties when they directly react with one another in a covalent cycloaddition reaction. The person skilled in the art would be able to select other functional group pairings capable of participating in cycloaddition reactions of this type that satisfy the requirements of click chemistry. In general thereof the identity of the R group will be chosen based on the relevant complementary R group on the biological entity of interest.

In some embodiments R is selected from the group consisting of —NCS, $CO_2H$, $NH_2$, an azide, an alkyne, an isonitrile, a tetrazine, maleimide, or a protected form thereof or a synthon thereof.

In some embodiments R is a moiety capable of taking part in a click chemistry reaction with a complementary moiety on a biological entity.

In some embodiments of the compounds of the invention the nitrogen containing macrocyclic metal ligand is complexed with a metal ion. The ligand may be complexed with any suitable metal ion and may be used to deliver a range of metal ions. In some embodiments the metal in the metal ion is selected from the group consisting of Cu, Tc, Gd, Ga, In, Co, Re, Fe, Au, Ag, Rh, Pt, Bi, Cr, W, Ni, V, Ir, Pt, Zn, Cd, Mn, Ru, Pd, Hg, and Ti.

In some embodiments the metal in the metal ion is a radionuclide selected from the group consisting of Cu, Tc, Ga, Co, In, Fe, and Ti. The present compounds have been found to be particularly applicable useful in binding copper ions. In some embodiments the metal in the metal ion is a radionuclide selected from the group consisting of $^{60}Cu$, $^{62}Cu$, $^{64}Cu$ and $^{67}Cu$. In some embodiments the metal in the metal ion is $^{60}Cu$. In some embodiments the metal in the metal ion is $^{62}Cu$. In some embodiments the metal in the metal ion is $^{64}Cu$. In some embodiments the metal in the metal ion is $^{67}Cu$.

The invention also relates to pharmaceutical compositions including a compound of the invention as described above and a pharmaceutically acceptable carrier, diluent or excipient.

These and other features of the present teachings are set forth herein.

DETAILED DESCRIPTION

In this specification a number of terms are used which are well known to a skilled addressee. Nevertheless for the purposes of clarity a number of terms will be defined.

As used herein, the term "unsubstituted" means that there is no substituent or that the only substituents are hydrogen.

The term "optionally substituted" as used throughout the specification denotes that the group may or may not be further substituted or fused (so as to form a condensed polycyclic system), with one or more non-hydrogen substituent groups. In certain embodiments the substituent groups are one or more groups independently selected from the group consisting of halogen, =O, =S, —CN, —$NO_2$, —$CF_3$, —$OCF_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, cycloalkylalkyl, heterocycloalkylalkyl, heteroarylalkyl, arylalkyl, cycloalkylalkenyl, heterocycloalkylalkenyl, arylalkenyl, heteroarylalkenyl, cycloalkylheteroalkyl, heterocycloalkylheteroalkyl, arylheteroalkyl, heteroarylheteroalkyl, hydroxy, hydroxyalkyl, alkyloxy, alkyloxyalkyl, alkyloxycycloalkyl, alkyloxyheterocycloalkyl, alkyloxyaryl, alkyloxyheteroaryl, alkyloxycarbonyl, alkylaminocarbonyl, alkenyloxy, alkynyloxy, cycloalkyloxy, cycloalkenyloxy, heterocycloalkyloxy, heterocycloalkenyloxy, aryloxy, phenoxy, benzyloxy, heteroaryloxy, arylalkyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, alkylsulfinyl, arylsulfinyl, aminosulfinylaminoalkyl, —C(=O)OH, —C(=O)$R^a$, —C(=O)$OR^a$, C(=O)$NR^aR^b$, C(=NOH)$R^a$, C(=$NR^a$)$NR^bR^c$, $NR^aR^b$, $NR^aC$(=O)$R^b$, $NR^aC$(=O)$OR^b$, $NR^aC$(=O)$NR^bR^c$, $NR^aC$(=$NR^b$)$NR^cR^d$, $NR^aSO_2R^b$, —$SR^a$, $SO_2NR^aR^b$, —$OR^a$, OC(=O)$NR^aR^b$, OC(=O)$R^a$ and acyl, wherein $R^a$, $R^b$, $R^c$ and $R^d$ are each independently selected from the group consisting of H, $C_1$-$C_{12}$alkyl, $C_1$-$C_{12}$haloalkyl, $C_2$-$C_{12}$alkenyl, $C_2$-$C_{12}$alkynyl, $C_2$-$C_{10}$heteroalkyl, $C_3$-$C_{12}$cycloalkyl, $C_3$-$C_{12}$cycloalkenyl, $C_2$-$C_{12}$heterocycloalkyl, $C_2$-$C_{12}$heterocycloalkenyl, $C_6$-$C_{18}$aryl, $C_1$-$C_{18}$heteroaryl, and acyl, or any two or more of $R^a$, $R^b$, $R^c$ and $R^d$, when taken together with the atoms to which they are attached form a heterocyclic ring system with 3 to 12 ring atoms.

In some embodiments each optional substituent is independently selected from the group consisting of: halogen, =O, =S, —CN, —$NO_2$, —$CF_3$, —$OCF_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkyloxy, alkyloxyalkyl, alkyloxyaryl, alkyloxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, amino, alkylamino, acylamino, aminoalkyl, arylamino, sulfonyl, alkylsulfonyl, arylsulfonyl, aminosulfonyl, aminoalkyl, —COOH, —SH, and acyl.

Examples of particularly suitable optional substituents include F, Cl, Br, I, $CH_3$, $CH_2CH_3$, OH, $OCH_3$, $CF_3$, $OCF_3$, $NO_2$, $NH_2$, and CN.

As used herein the term "amino acid" refers to a molecule which contains both an amine and a carboxyl function. The amino acid may be a natural or an unnatural amino acid.

"Alkenyl" as a group or part of a group denotes an aliphatic hydrocarbon group containing at least one carbon-carbon double bond and which may be straight or branched preferably having 2-12 carbon atoms, more preferably 2-10 carbon atoms, most preferably 2-6 carbon atoms, in the normal chain. The group may contain a plurality of double bonds in the normal chain and the orientation about each is independently E or Z. Exemplary alkenyl groups include, but are not limited to, ethenyl, propenyl, butenyl, pentenyl, hexenyl, heptenyl, octenyl and nonenyl. The group may be a terminal group or a bridging group.

"Alkyl" as a group or part of a group refers to a straight or branched aliphatic hydrocarbon group, preferably a $C_1$-$C_{12}$ alkyl, more preferably a $C_1$-$C_{10}$ alkyl, most preferably $C_1$-$C_6$ unless otherwise noted. Examples of suitable straight and branched $C_1$-$C_6$ alkyl substituents include methyl, ethyl, n-propyl, 2-propyl, n-butyl, sec-butyl, t-butyl, hexyl, and the like. The group may be a terminal group or a bridging group.

"Alkynyl" as a group or part of a group means an aliphatic hydrocarbon group containing a carbon-carbon triple bond and which may be straight or branched preferably having from 2-12 carbon atoms, more preferably 2-10 carbon atoms, more preferably 2-6 carbon atoms in the normal chain. Exemplary structures include, but are not limited to, ethynyl and propynyl. The group may be a terminal group or a bridging group.

"Aryl" as a group or part of a group denotes (i) an optionally substituted monocyclic, or fused polycyclic, aromatic carbocycle (ring structure having ring atoms that are all carbon) preferably having from 5 to 12 atoms per ring. Examples of aryl groups include phenyl, naphthyl, and the like; (ii) an optionally substituted partially saturated bicyclic aromatic carbocyclic moiety in which a phenyl and a $C_{5-7}$ cycloalkyl or $C_{5-7}$ cycloalkenyl group are fused together to form a cyclic structure, such as tetrahydronaphthyl, indenyl or indanyl. The group may be a terminal group or a bridging group. Typically an aryl group is a $C_6$-$C_{18}$ aryl group.

"Cycloalkyl" refers to a saturated monocyclic or fused or spiro polycyclic, carbocycle preferably containing from 3 to 9 carbons per ring, such as cyclopropyl, cyclobutyl, cyclopentyl, cyclohexyl and the like, unless otherwise specified. It includes monocyclic systems such as cyclopropyl and cyclohexyl, bicyclic systems such as decalin, and polycyclic systems such as adamantane. A cycloalkyl group typically is a $C_3$-$C_9$ cycloalkyl group. The group may be a terminal group or a bridging group.

"Halogen" represents chlorine, fluorine, bromine or iodine.

"Heteroalkyl" refers to a straight- or branched-chain alkyl group preferably having from 2 to 12 carbons, more preferably 2 to 6 carbons in the chain, in which one or more of the carbon atoms (and any associated hydrogen atoms) are each independently replaced by a heteroatomic group selected from S, O, P and NR' where R' is selected from the group consisting of H, optionally substituted $C_1$-$C_{12}$alkyl, optionally substituted $C_3$-$C_{12}$cycloalkyl, optionally substituted $C_6$-$C_{18}$aryl, and optionally substituted $C_1$-$C_{18}$heteroaryl. Exemplary heteroalkyls include alkyl ethers, secondary and tertiary alkyl amines, amides, alkyl sulfides, and the like. Examples of heteroalkyl also include hydroxy$C_1$-$C_6$alkyl, $C_1$-$C_6$alkyloxy$C_1$-$C_6$alkyl, amino$C_1$-$C_6$alkyl, $C_1$-$C_6$alkylamino$C_1$-$C_6$alkyl, and di($C_1$-$C_6$alkyl)amino$C_1$-$C_6$alkyl. The group may be a terminal group or a bridging group.

"Heteroaryl" either alone or part of a group refers to groups containing an aromatic ring (preferably a 5 or 6 membered aromatic ring) having one or more heteroatoms as ring atoms in the aromatic ring with the remainder of the ring atoms being carbon atoms. Suitable heteroatoms include nitrogen, oxygen and sulphur. Examples of heteroaryl include thiophene, benzothiophene, benzofuran, benzimidazole, benzoxazole, benzothiazole, benzisothiazole, naphtho[2,3-b]thiophene, furan, isoindolizine, xantholene, phenoxatine, pyrrole, imidazole, pyrazole, pyridine, pyrazine, pyrimidine, pyridazine, tetrazole, indole, isoindole, 1H-indazole, purine, quinoline, isoquinoline, phthalazine, naphthyridine, quinoxaline, cinnoline, carbazole, phenanthridine, acridine, phenazine, thiazole, isothiazole, phenothiazine, oxazole, isooxazole, furazane, phenoxazine, 2-, 3- or 4-pyridyl, 2-, 3-, 4-, 5-, or 8-quinolyl, 1-, 3-, 4-, or 5-isoquinolinyl 1-, 2-, or 3-indolyl, and 2-, or 3-thienyl. A heteroaryl group is typically a $C_1$-$C_{18}$ heteroaryl group. The group may be a terminal group or a bridging group.

The term "normal chain" refers to the direct chain joining the two ends of a linking moiety.

The term "pharmaceutically acceptable salts" refers to salts that retain the desired biological activity of the above-identified compounds, and include pharmaceutically acceptable acid addition salts and base addition salts. Suitable pharmaceutically acceptable acid addition salts of compounds of Formula (I) may be prepared from an inorganic acid or from an organic acid. Examples of such inorganic acids are hydrochloric, sulfuric, and phosphoric acid. Appropriate organic acids may be selected from aliphatic, cycloaliphatic, aromatic, heterocyclic carboxylic and sulfonic classes of organic acids, examples of which are formic, acetic, propionic, succinic, glycolic, gluconic, lactic, malic, tartaric, citric, fumaric, maleic, alkyl sulfonic, arylsulfonic. Additional information on pharmaceutically acceptable salts can be found in *Remington's Pharmaceutical Sciences,* 19th Edition, Mack Publishing Co., Easton, Pa. 1995. In the case of agents that are solids, it is understood by those skilled in the art that the inventive compounds, agents and salts may exist in different crystalline or polymorphic forms, all of which are intended to be within the scope of the present invention and specified formulae.

The term "therapeutically effective amount" or "effective amount" is an amount sufficient to effect beneficial or desired clinical results. An effective amount can be administered in one or more administrations. An effective amount is typically sufficient to palliate, ameliorate, stabilize, reverse, slow or delay the progression of the disease state. An effective amount for radioimaging is typically sufficient to identify the radionuclide in the subject.

The term 'click chemistry' is used to describe covalent reactions with high reaction yields that can be performed under extremely mild conditions. A number of 'click' reactions involve a cycloaddition reaction between appropriate functional groups to generate a stable cyclic structure. The most well documented click reaction is the Cu(I) catalyzed variant of the Huisgen 1,3-dipolar cycloaddition of azides and alkynes to form 1,2,3-triazoles. Many click reactions are thermodynamically driven, leading to fast reaction times, high product yields and high selectivity in the reaction.

The compounds and methods of the invention as discussed above may include a wide variety of nitrogen containing macrocyclic metal ligands.

The ligand may be a monocyclic nitrogen containing metal ligand based on the cyclam or cyclen frameworks. Ligand of this type and derivatives thereof may be synthesised using methodology available in the art such as in Bernhardt (J. Chem. Soc., Dalton Transactions, 1996, pages 4319-4324), Bernhardt et al (J. Chem. Soc., Dalton Transactions, 1996, pages 4325-4330), and Bernhardt and Sharpe (Inorg Chem, 2000, 39, pages 2020-2025). Various other ligands of this general type may be made by variation of the procedures described in these articles.

The ligand may also be a cage like cryptand ligand as described for example in Geue (Chemical communications, 1994, page 667). Cryptand ligands of this type are described in U.S. Pat. No. 4,497,737 in the name of Sargeson et al, the disclosure of which is incorporated herein by reference.

The synthesis involves a metal ion template reaction and involves condensation of a tris-(diamine) metal ion complex (see column 3 lines 30 to 35) with formaldehyde and an appropriate nucleophile in the presence of base. The identity of the nucleophile will determine the identity of the substituents on the cage ligand and a skilled addressee can access a wide variety of substitution patterns around the cage ligand by judicious choice of the appropriate amine used in the condensation as well as the identity of the nucleophile.

In order to produce the compounds of formula (2) of the invention the amino substituted ligand or a metal complexed form thereof is reacted with an appropriate compound of formula (1) under suitable reaction conditions to arrive at the final product.

Whilst the reaction may be performed on the free ligand there is still a possibility of the reaction being compromised by the presence of the ring nitrogen(s). As such it is desirable to perform the reaction using a metal complex thereof as the metal serves to act as a protecting group for the secondary nitrogen atoms in the ring. Whilst any suitable metal can be used the metal is typically selected from copper and magnesium. In one embodiment the metal is copper. In another embodiment the metal is magnesium.

In addition depending upon the substituents on amino substituted ligand it may be necessary to protect the substituents from interfering with the reaction. For example the applicants have found that where the ligand contains more than one free amino group (such as will be the case if the original ligand was 1,8-diamino-Sar) then it may be desirable to first protect one of the amino groups prior to reaction with a suitable nitrogen protecting group. An example of a suitable protecting group of this type is the acetyl group.

The reaction may be carried out in any suitable solvent which is inert to the two reactants with the identity of the solvent being determined by the relative solubilities of the thiocyanate and the amine substituted metal ligand. Examples of solvents that may be used include aliphatic, aromatic, or halogenated hydrocarbons such as benzene, toluene, xylenes; chlorobenzene, chloroform, methylene chloride, ethylene chloride; ethers and ethereal compounds such as dialkyl ether, ethylene glycol mono or-dialkyl ether, THF, dioxane; nitriles such as acetonitrile or 2-methoxypropionitrile; N,N-dialkylated amides such as dimethylformamide; and dimethyl acetamide, dimethylsulphoxide, tetramethylurea; as well as mixtures of these solvents with each other.

The reaction may be carried out at any of a number of suitable temperatures with the reaction temperature being able to be readily determined on a case by case basis. Nevertheless the reaction temperature is typically carried out at from 0 to 100° C., more typically 50 to 80° C.

The reaction may be carried out using a wide variety of compounds of formula (1);

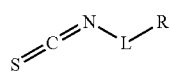
(1)

In choosing a suitable compound of formula (1) the skilled addressee in the art will take into account the desired moiety capable of binding to a biological entity that they intend to introduce or attach to the ligand. This will guide them in their choice of L and R.

The exact compound produced will depend upon the reaction stoichiometry and the starting materials with a skilled addressee being able to adjust either of these variables to produce the desired final product.

Examples of compounds of formula (2) that may be produced using the methodology described above include:

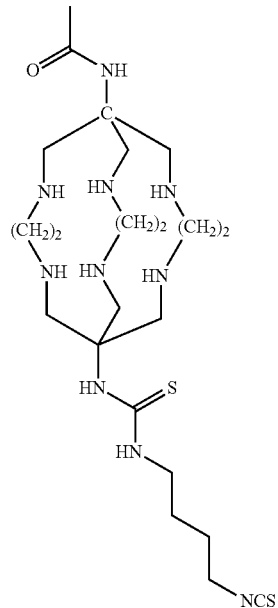

-continued

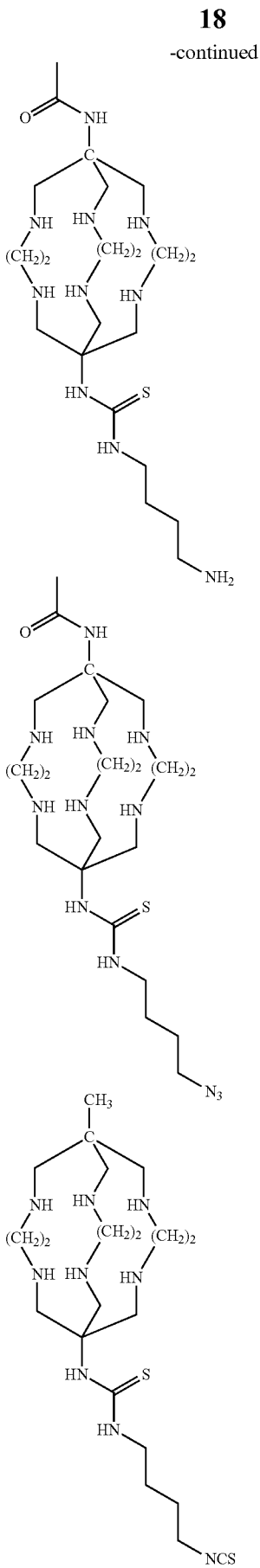

19
-continued
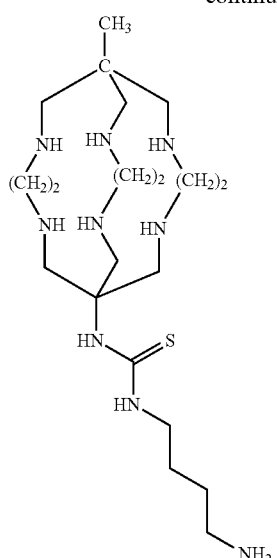
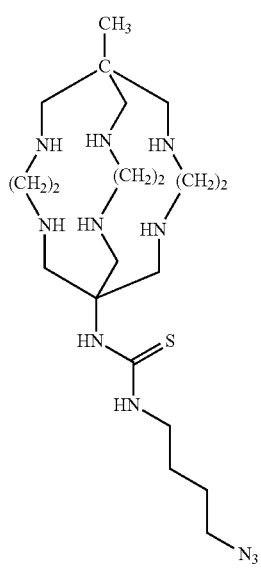
20
-continued
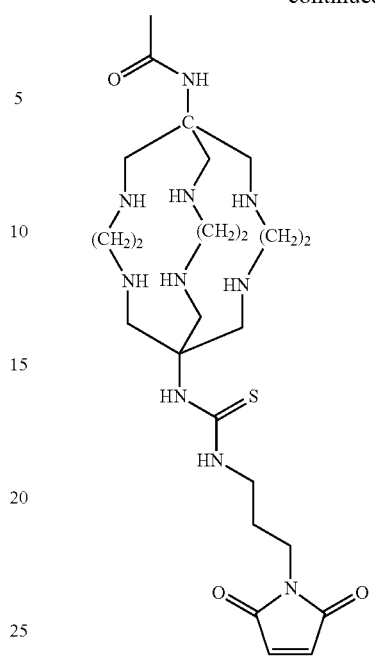
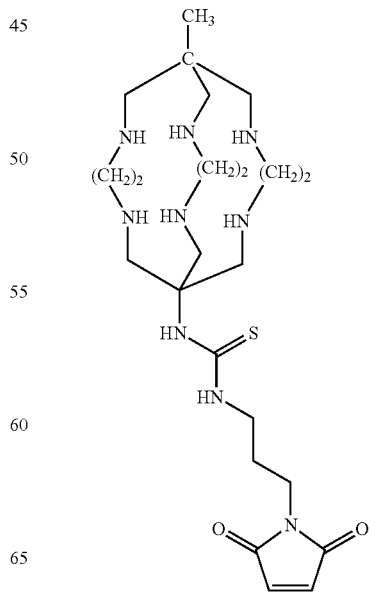

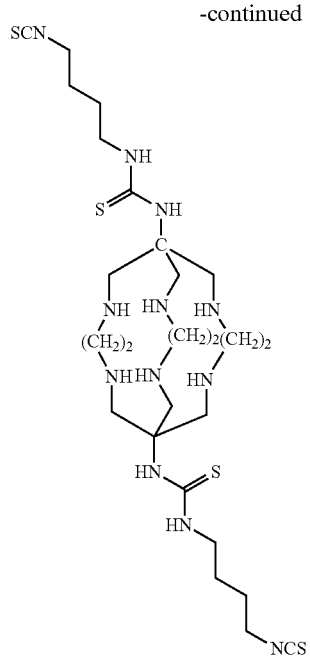
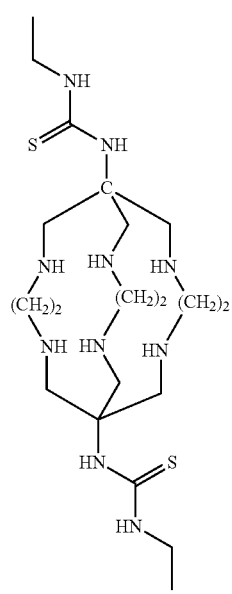
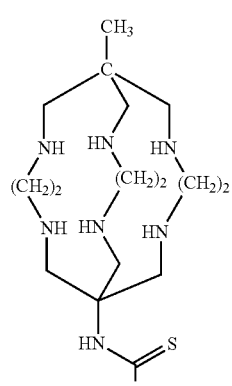
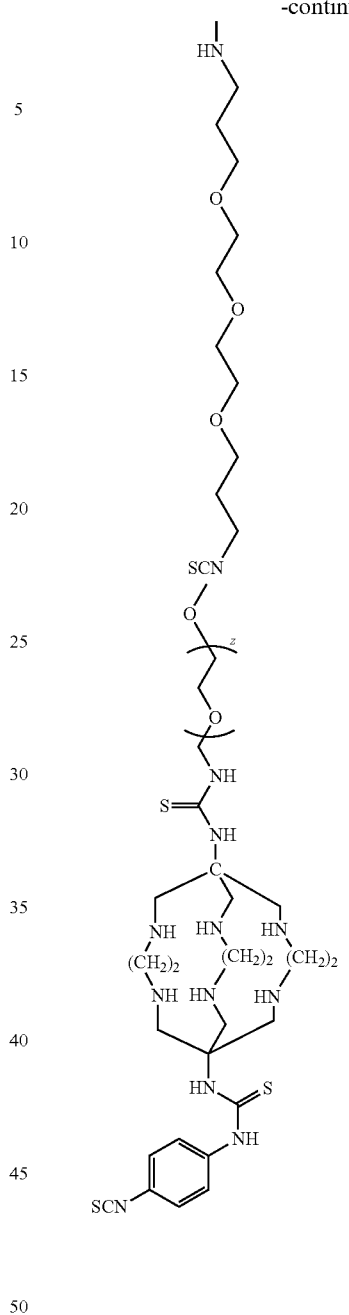
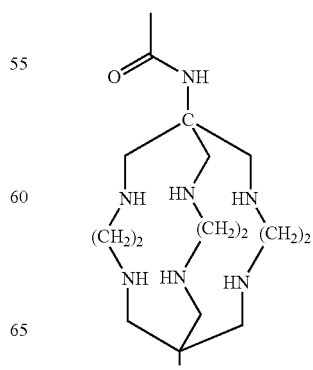

23
-continued
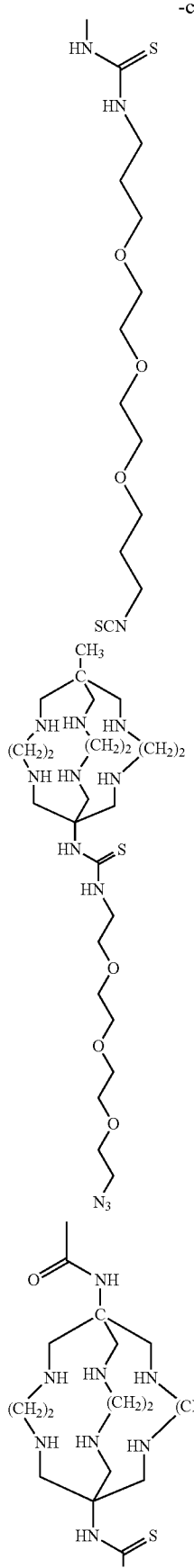
24
-continued
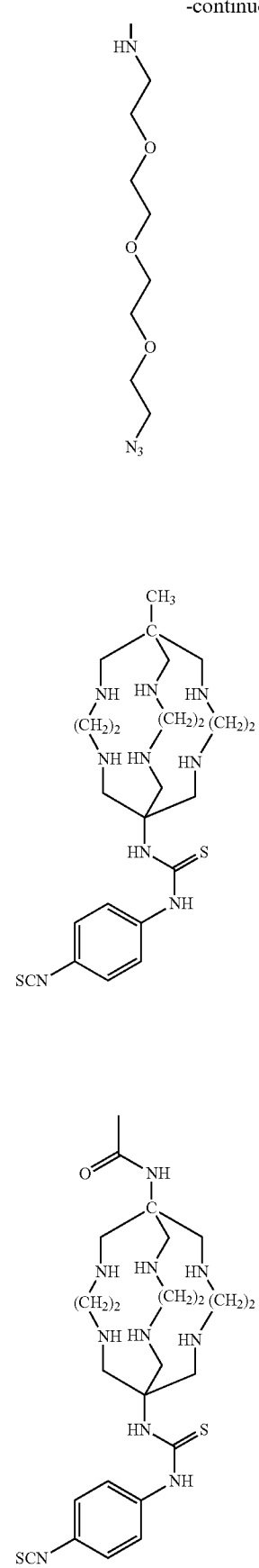

25
-continued
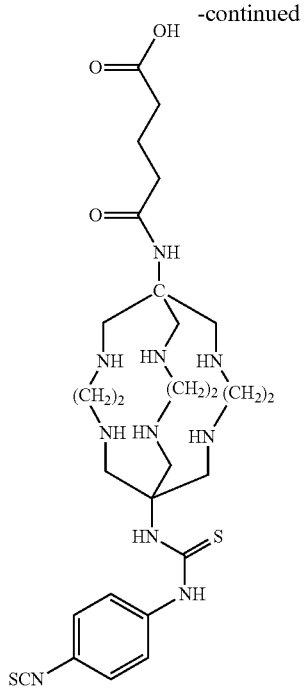
26
-continued
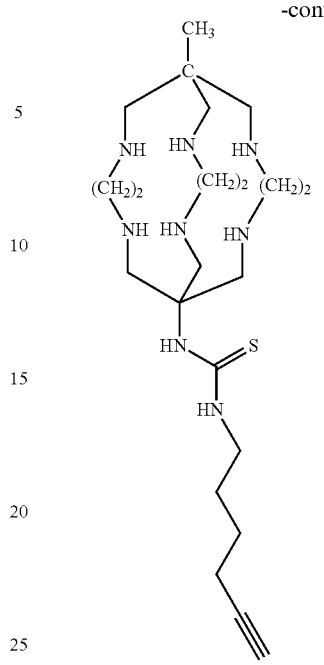
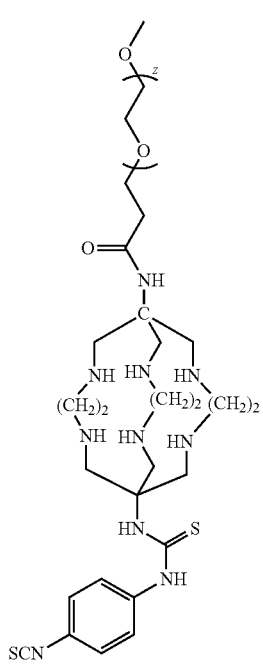
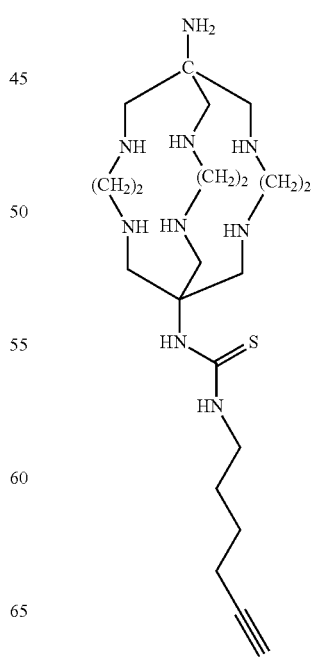

27
-continued
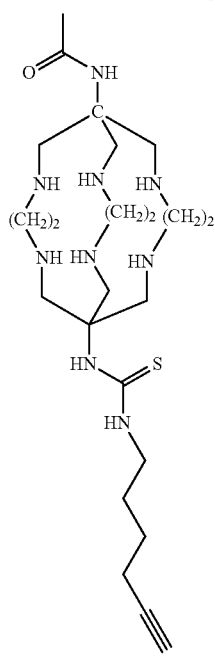
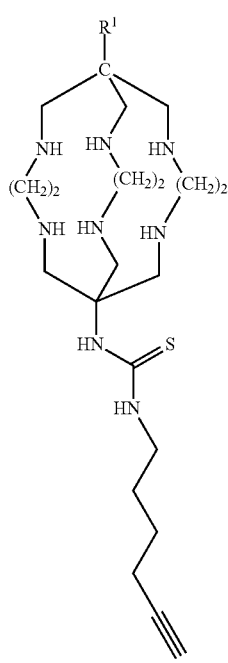
28
-continued
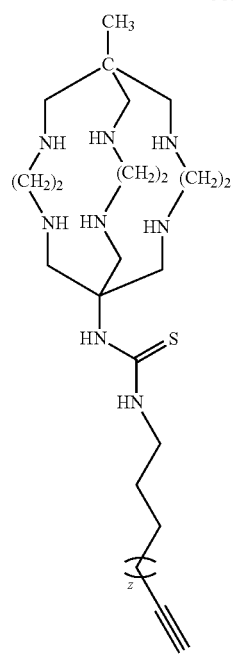
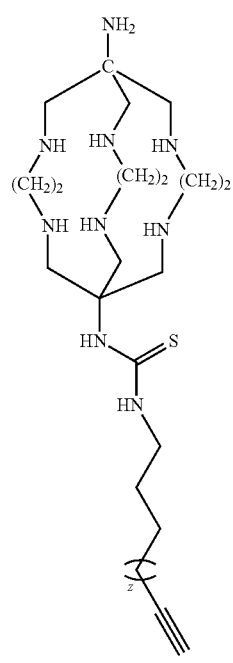

29
-continued
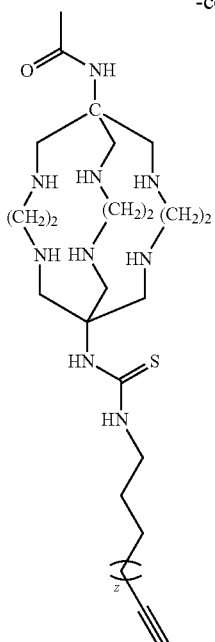
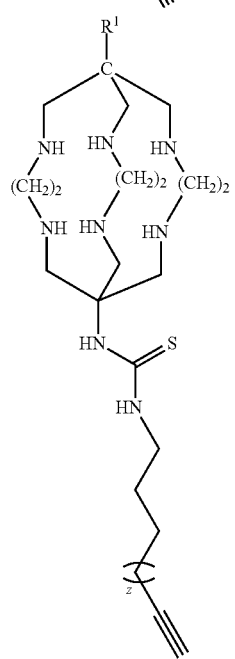
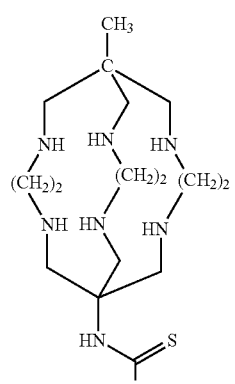
30
-continued
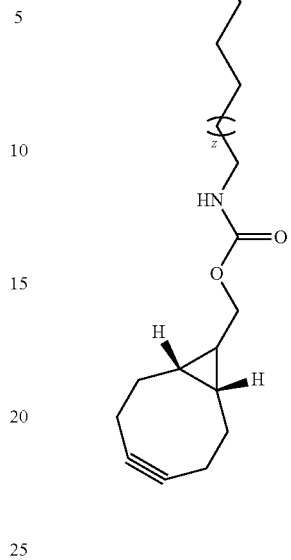
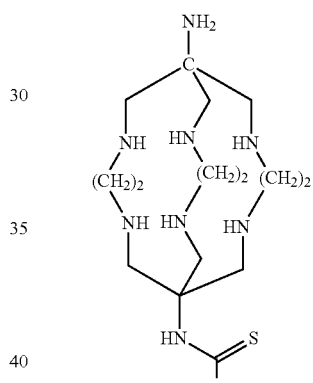
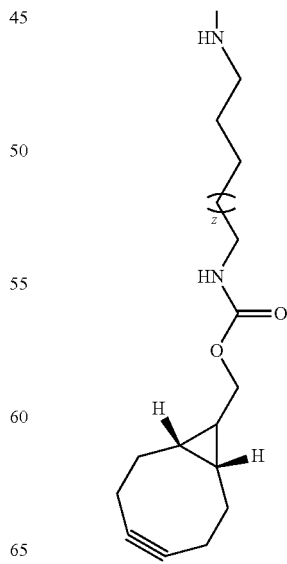

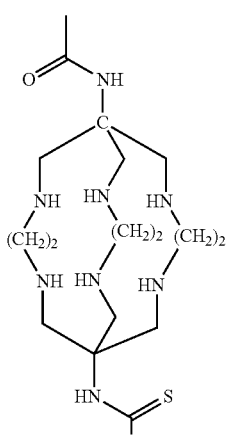
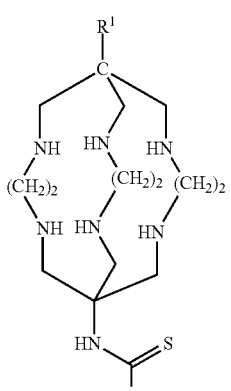
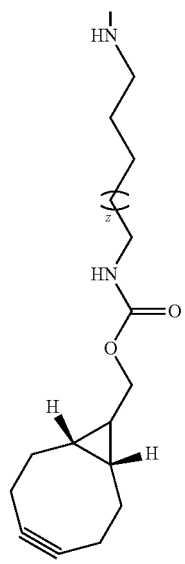
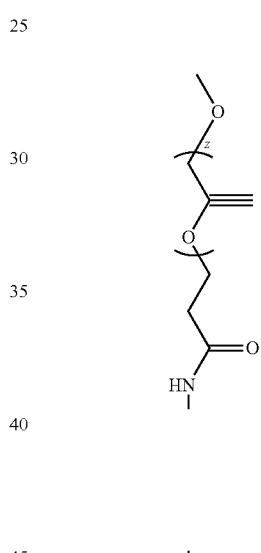
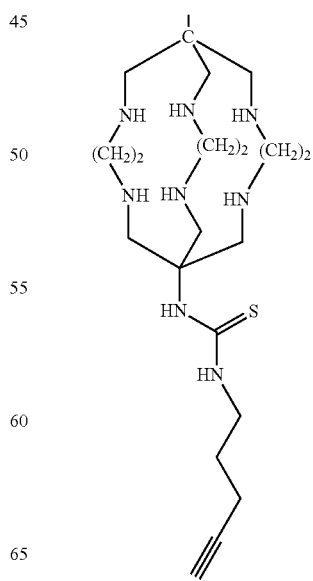

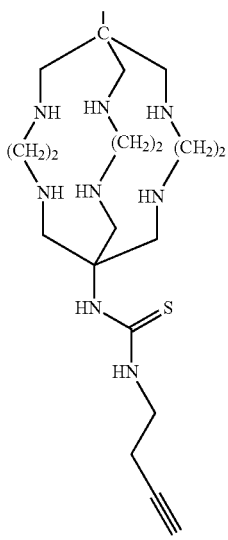

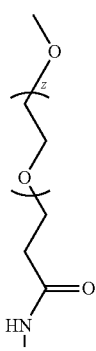

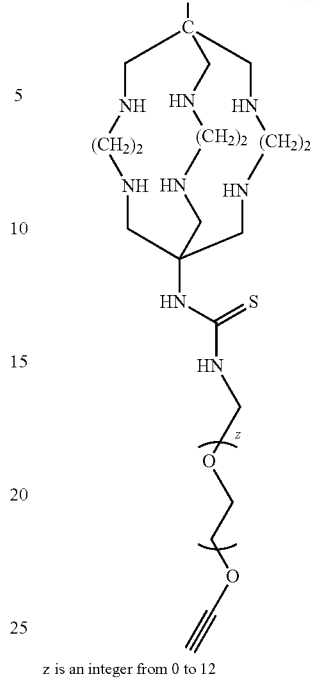

z is an integer from 0 to 12 or a metal complex thereof.

These compounds may then be further elaborated to produce compounds of interest by reacting the reactive moiety with a suitable reactive element on a biological element. Thus for example where the R is a moiety capable of taking part in a click chemistry reaction with a complementary moiety on a biological entity the R group will be chosen depending upon the moieties on the biological entity of interest.

The R group may also react or bind to the biological entity by reaction with a pendant moiety on the biological entity (either naturally present or by modification of the biological entity). Once again a skilled worked in the field will be able to review the biological entity of interest in any specific circumstance and determine a suitable R group to bind to the pendant moieties on the R group.

The formation of the metal complexes of the compounds synthesised in this way is carried out using techniques well known in the art.

As discussed above the compounds of the invention are useful as they can bind to a biological entity. The compounds of formula (2) containing a radionuclide complexed with the ligand may be used in either radiotherapy or in diagnostic imaging applications. In each instance both therapy and diagnostic imaging will rely on the binding to the biological entity being involved in facilitating the localisation of the complex containing the radionuclide in the desired tissues or organs of the subject being treated/imaged.

Thus for example in relation to the use of the radiolabelled compounds of formula (2) it is anticipated that these will be used by first binding them to a biological entity of interest followed by administration of an effective amount of the radiolabelled compound to a subject followed by monitoring of the subject after a suitable time period to determine if the radiolabelled compound has localised at a particular location in the body or whether the compound is broadly speaking evenly distributed through the body. As a general rule where the radio labelled compound is localised in tissue or an organ of the body this is indicative of the presence in that tissue or organ of something that is recognised by the particular molecular recognition moiety used.

Accordingly judicious selection of a biological entity to connect the compound of formula (2) to is important in determining the efficacy of any of the radiolabelled compounds of the invention in diagnostic imaging applications. In this regard a wide range of biological entities that can act as molecular recognition moieties are known in the art which are well characterised and which are known to selectively target certain receptors in the body. In particular a number of biological entities that can act as molecular recognition moieties or molecular recognition portions are known that target tissue or organs when the patient is suffering from certain medical conditions. Examples of biological entities that can act as molecular recognition moieties or molecular recognition portions that are known and may be used in this invention include Octreotate, octreotide, [Tyr$^3$]-octreotate, [Tyr$^1$]-octreotate, bombesin, bombesin(7-14), gastrin releasing peptide, single amino acids, penetratin, annexin V, TAT, cyclic RGD, glucose, glucosamine (and extended carbohydrates), folic acid, neurotensin, neuropeptide Y, cholecystokinin (CCK) analogues, vasoactive intestinal peptide (VIP), substance P, alpha-melanocyte-stimulating hormone (MSH). For example, certain cancers are known to over express somatostatin receptors and so the molecular recognition moiety may be one which targets these receptors. An example of a molecular recognition moieties or molecular recognition portions of this type is [Tyr$^3$]-octreotate. Another example of a molecular recognition moieties or molecular recognition portions is cyclic RGD which is an integrin targeting cyclic peptide. In other examples a suitable molecular recognition moieties or molecular recognition portions is bombesin which is known to target breast and pancreatic cancers.

The monitoring of the subject for the location of the radiolabelled material will typically provide the analyst with information regarding the location of the radiolabelled material and hence the location of any material that is targeted by the molecular recognition moiety (such as cancerous tissue). An effective amount of the compounds of the invention will depend upon a number of factors and will of necessity involve a balance between the amount of radioactivity required to achieve the desired radio imaging effect and the general interest in not exposing the subject (or their tissues or organs) to any unnecessary levels of radiation which may be harmful.

The methods of treatment of the present invention involve administration of a compound of formula (2) which has been bound to a suitable biological entity and complexed to a radionuclide. The compounds of formula (2) after being bound to a biological entity are able to deliver the radionuclide to the desired location in the body where its mode of action is desired. As discussed above examples of suitable biological entities to act as molecular recognition moieties are known in the art and a skilled artisan can select the appropriate molecular recognition moiety to target the desired tissue in the body to be treated.

A therapeutically effective amount can be readily determined by an attending clinician by the use of conventional techniques and by observing results obtained under analogous circumstances. In determining the therapeutically effective amount a number of factors are to be considered including but not limited to, the species of animal, its size, age and general health, the specific condition involved, the severity of the condition, the response of the patient to treatment, the particular radio labelled compound administered, the mode of administration, the bioavailability of the preparation administered, the dose regime selected, the use of other medications and other relevant circumstances.

In addition the treatment regime will typically involve a number of cycles of radiation treatment with the cycles being continued until such time as the condition has been ameliorated. Once again the optimal number of cycles and the spacing between each treatment cycle will depend upon a number of factors such as the severity of the condition being treated, the health (or lack thereof) of the subject being treated and their reaction to radiotherapy. In general the optimal dosage amount and the optimal treatment regime can be readily determined by a skilled addressee in the art using well known techniques.

In using the compounds of the invention they can be administered in any form or mode which makes the compound available for the desired application (imaging or radio therapy). One skilled in the art of preparing formulations of this type can readily select the proper form and mode of administration depending upon the particular characteristics of the compound selected, the condition to be treated, the stage of the condition to be treated and other relevant circumstances. We refer the reader to *Remingtons Pharmaceutical Sciences,* 19$^{th}$ edition, Mack Publishing Co. (1995) for further information.

The compounds of the present invention can be administered alone or in the form of a pharmaceutical composition in combination with a pharmaceutically acceptable carrier, diluent or excipient. The compounds of the invention, while effective themselves, are typically formulated and administered in the form of their pharmaceutically acceptable salts as these forms are typically more stable, more easily crystallised and have increased solubility.

The compounds are, however, typically used in the form of pharmaceutical compositions which are formulated depending on the desired mode of administration. The compositions are prepared in manners well known in the art.

The invention in other embodiments provides a pharmaceutical pack or kit comprising one or more containers filled with one or more of the ingredients of the pharmaceutical compositions of the invention. In such a pack or kit can be found at least one container having a unit dosage of the agent(s). Conveniently, in the kits, single dosages can be provided in sterile vials so that the clinician can employ the vials directly, where the vials will have the desired amount and concentration of compound and radio nucleotide which may be admixed prior to use. Associated with such container(s) can be various written materials such as instructions for use, or a notice in the form prescribed by a governmental agency regulating the manufacture, use or sale of pharmaceuticals, imaging agents or biological products, which notice reflects approval by the agency of manufacture, use or sale for human administration.

The compounds of the invention may be used or administered in combination with one or more additional drug(s) that are anti-cancer drugs and/or procedures (e.g. surgery, radiotherapy) for the treatment of the disorder/diseases mentioned. The components can be administered in the same formulation or in separate formulations. If administered in separate formulations the compounds of the invention may be administered sequentially or simultaneously with the other drug(s).

In addition to being able to be administered in combination with one or more additional drugs that include anti-cancer drugs, the compounds of the invention may be used in a combination therapy. When this is done the compounds are typically administered in combination with each other. Thus one or more of the compounds of the invention may be administered either simultaneously (as a combined preparation) or sequentially in order to achieve a desired effect. This is especially desirable where the therapeutic profile of each compound is different such that the combined effect of the two drugs provides an improved therapeutic result.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of micro-organisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents that delay absorption such as aluminium monostearate and gelatin.

If desired, and for more effective distribution, the compounds can be incorporated into slow release or targeted delivery systems such as polymer matrices, liposomes, and microspheres.

The injectable formulations can be sterilized, for example, by filtration through a bacterial-retaining filter, or by incorporating sterilizing agents in the form of sterile solid compositions that can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

If desired, and for more effective distribution, the compounds can be incorporated into slow release or targeted delivery systems such as polymer matrices, liposomes, and microspheres.

The active compounds can also be in microencapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminium metahydroxide, bentonite, agar-agar, and tragacanth, and mixtures thereof.

As discussed above, the compounds of the embodiments may be useful for treating and/or detecting proliferative diseases. Examples of such cell proliferative diseases or conditions include cancer (include any metastases), psoriasis, and smooth muscle cell proliferative disorders such as restenosis. The compounds of the present invention may be particularly useful for treating and/or detecting tumours such as breast cancer, colon cancer, lung cancer, ovarian cancer, prostate cancer, head and/or neck cancer, or renal, gastric, pancreatic cancer and brain cancer as well as hematologic malignancies such as lymphoma and leukaemia. In addition, the compounds of the present invention may be useful for treating and/or detecting a proliferative disease that is refractory to the treatment and/or detecting with other anti-cancer drugs; and for treating and/or detecting hyperproliferative conditions such as leukaemia's, psoriasis and restenosis. In other embodiments, compounds of this invention can be used to treat and/or detect pre-cancer conditions or hyperplasia including familial adenomatous polyposis, colonic adenomatous polyps, myeloid dysplasia, endometrial dysplasia, endometrial hyperplasia with atypia, cervical dysplasia, vaginal intraepithelial neoplasia, benign prostatic hyperplasia, papillomas of the larynx, actinic and solar keratosis, seborrheic keratosis and keratoacanthoma.

SYNTHESIS OF COMPOUNDS OF THE INVENTION

The agents of the various embodiments may be prepared using the reaction routes and synthesis schemes as described below, employing the techniques available in the art using starting materials that are readily available. In general the ligand containing one or more free amines (depending upon whether you want a dimer or not) is reacted with a suitable compound of formula (1) as shown in example 1 under appropriate conditions to either form the mono functionalized ligand or a di-functionalised ligand (when a dimer is preferred and a di-amino ligand is the starting material). The preparation of particular compounds of the embodiments is described in detail in the following examples, but the artisan will recognize that the chemical reactions described may be readily adapted to prepare a number of other agents of the various embodiments. For example, the synthesis of non-exemplified compounds may be successfully performed by modifications apparent to those skilled in the art, e.g. by appropriately protecting interfering groups, by changing to other suitable reagents known in the art, or by making routine modifications of reaction conditions. A list of suitable protecting groups in organic synthesis can be found in T. W. Greene's Protective Groups in Organic Synthesis, 3$^{rd}$ Edition, John Wiley & Sons, 1991. Alternatively, other reactions disclosed herein or known in the art will be recognized as having applicability for preparing other compounds of the various embodiments.

Reagents useful for synthesizing compounds may be obtained or prepared according to techniques known in the art.

EXAMPLES

In the examples described below, unless otherwise indicated, all temperatures in the following description are in degrees Celsius and all parts and percentages are by weight, unless indicated otherwise.

Various starting materials and other reagents were purchased from commercial suppliers, such as Aldrich Chemical Company or Lancaster Synthesis Ltd., and used without further purification, unless otherwise indicated. Tetrahydrofuran (THF) and N,N-dimethylformamide (DMF) were purchased from Aldrich in SureSeal bottles and used as received. All solvents were purified by using standard methods in the art, unless otherwise indicated. SP Sephadex C25 and DOWEX 50wx2 200-400 mesh cation exchange resin was purchased from Aldrich. Fmoc-L-amino acids, HATU, HCTU and 2-chlorotrityl resin were purchased from GL Biochem Ltd (Shanghai, China). Fmoc-Lys(iv-Dde)-OH and Fmoc-D-amino acids were purchased from Bachem AG (Switzerland). Fmoc-Pal-PEG-PS resin was purchased from Applied Biosystems (Foster City, Calif.). Nova PEG Rink Amide resin was purchased from NovaBiochem, Darmstadt, Germany. [Co((NO$_2$)$_2$sar)]Cl$_3$, [Co((NH$_2$)$_2$sar)]Cl$_3$, (NH$_2$)$_2$sar, [Cu(NH$_3$)$_2$sar](CF$_3$SO$_3$)$_4$ were prepared according to established procedures. (1) Geue, R. J.; Hambley, T. W.; Harrowfield, J. M.; Sargeson, A. M.; Snow, M. R. *J. Am. Chem. Soc.* 1984, 106, 5478-5488. (2) Bottomley, G. A.; Clark, I. J.; Creaser, I. I.; Engelhardt, L. M.; Geue, R. J.; Hagen, K. S.; Harrowfield, J. M.; Lawrance, G. A.; Lay, P. A.; Sargeson, A. M.; See, A. J.; Skelton, B. W.; White, A. H.; Wilner, F. R. Aust. *J. Chem.* 1994, 47, 143-179 and (3) Bernhardt, P. V.; Bramley, R.; Engelhardt, L. M.; Harrowfield, J. M.; Hockless, D. C. R.; Korybut-Daszkiewicz, B. R.; Krausz, E. R.; Morgan, T.; Sargeson, A. M.; Skelton, B. W.; White, A. H. *Inorg. Chem.* 1995, 34, 3589-3599.

The reactions set forth below were performed under a positive pressure of nitrogen, argon or with a drying tube, at ambient temperature (unless otherwise stated), in anhydrous solvents, and the reaction flasks are fitted with rubber septa for the introduction of substrates and reagents via syringe. Glassware was oven-dried and/or heat-dried.

Work-ups were typically done by doubling the reaction volume with the reaction solvent or extraction solvent and then washing with the indicated aqueous solutions using 25% by volume of the extraction volume (unless otherwise indicated). Product solutions were dried over anhydrous sodium sulfate prior to filtration, and evaporation of the solvents was under reduced pressure on a rotary evaporator and noted as solvents removed in vacuo. Flash column chromatography [Still et al, *J. Org. Chem.*, 43, 2923 (1978)] was conducted using E Merck-grade flash silica gel (47-61 mm) and a silica gel:crude material ratio of about 20:1 to 50:1, unless otherwise stated. Hydrogenolysis was done at the pressure indicated or at ambient pressure.

Mass spectra were recorded in the positive ion mode on an Agilent 6510 Q-TOF LC/MS Mass Spectrometer coupled to an Agilent 1100 LC system (Agilent, Palo Alto, Calif.). Data were acquired and reference mass corrected via a dual-spray electrospray ionisation source, using the factory-defined calibration procedure. Each scan or data point on the Total Ion Chromatogram is an average of 9652 transients, producing 1.02 scans s$^{-1}$. Spectra were created by averaging the scans across each peak. Mass spectrometer conditions: fragmentor: 200-300 V; drying gas flow: 7 L/min; nebuliser: 30 psi; drying gas temp: 325° C.; V$_{cap}$: 4000 V; skimmer: 65 V; OCT R$_f$V: 750 V; scan range acquired: 150-3000 m/z.

HPLC-MS traces were recorded using an Agilent Eclipse Plus C18 column (5 µm, 2.1×150 mm) coupled to the Agilent 6510 Q-TOF LC/MS Mass Spectrometer described above. 1 µL aliquots of each sample were injected onto the column using the Agilent 1100 LC system, with a flow rate of 0.5 mL/min. Data acquisition parameters are the same as those described above for mass spectra, with the exception of the fragmentor (fragmentor voltage: 100 V).

NMR spectra were recorded on a Varian FT-NMR 500 spectrometer operating at 500 MHz for $^1$H NMR and 125.7 MHz for $^{13}$C-NMR. NMR spectra are obtained as D$_2$O solutions (reported in ppm), using acetone as the reference standard (2.22 ppm and 30.89 ppm respectively). Other NMR solvents were used as needed. When peak multiplicities are reported, the following abbreviations are used: s=singlet, d=doublet, t=triplet, m=multiplet, br=broadened, dd=doublet of doublets, dt=doublet of triplets. Coupling constants, when given, are reported in Hertz.

Semi-preparative HPLC purifications were performed using an Agilent 1200 Series HPLC system with a 5 mL/min flow rate. Solvent gradients and column specifications are described in the examples. An automated Agilent 1200 fraction collector collected 1-3 mL fractions and fraction collection was based on UV-Vis detection at 214 or 220 nm, with a lower threshold limit between 100-400 mAU. Each fraction was analysed using MS and analytical HPLC.

Analytical HPLC traces were acquired using an Agilent 1200 Series HPLC system and an Agilent Zorbax Eclipse XDB-C18 column (4.6×150 mm, 5 µm) with a 1 mL/min flow rate and UV spectroscopic detection at 214 nm, 220 nm and 270 nm.

UV-Vis spectra were acquired on a Cary 300 Bio UV-Vis spectrophotometer, from 800-200 nm at 0.500 nm data intervals with a 300.00 nm/min scan rate.

Voltametric experiments were performed with an Autolab (Eco Chemie, Utrecht, Netherlands) computer-controlled electrochemical workstation. A standard three-electrode arrangement was used with a glassy carbon disk (d, 3 mm) as working electrode, a Pt wire as auxiliary electrode and a Ag/AgCl reference electrode (silver wire in H$_2$O (KCl (0.1 M) AgNO$_3$ (0.01 M)). Scan rate: 100 mV/s, sample interval: 1.06 mV, sensitivity: 1×10$^{-4}$ A.

HPLC traces of radiolabelled peptides were acquired using a Waters Comosil C18 column (4.6×150 mm) coupled to a Shimadzu LC-20AT with a sodium iodide scintillation detector and a UV-Vis detector. 100 µL aliquots of each radiolabelled sample were injected onto the column, using a flow rate of 1 mL/min.

The following examples are intended to illustrate the embodiments disclosed and are not to be construed as being limitations thereto. Additional compounds, other than those described below, may be prepared using the following described reaction scheme or appropriate variations or modifications thereof.

Example 1 CuL²

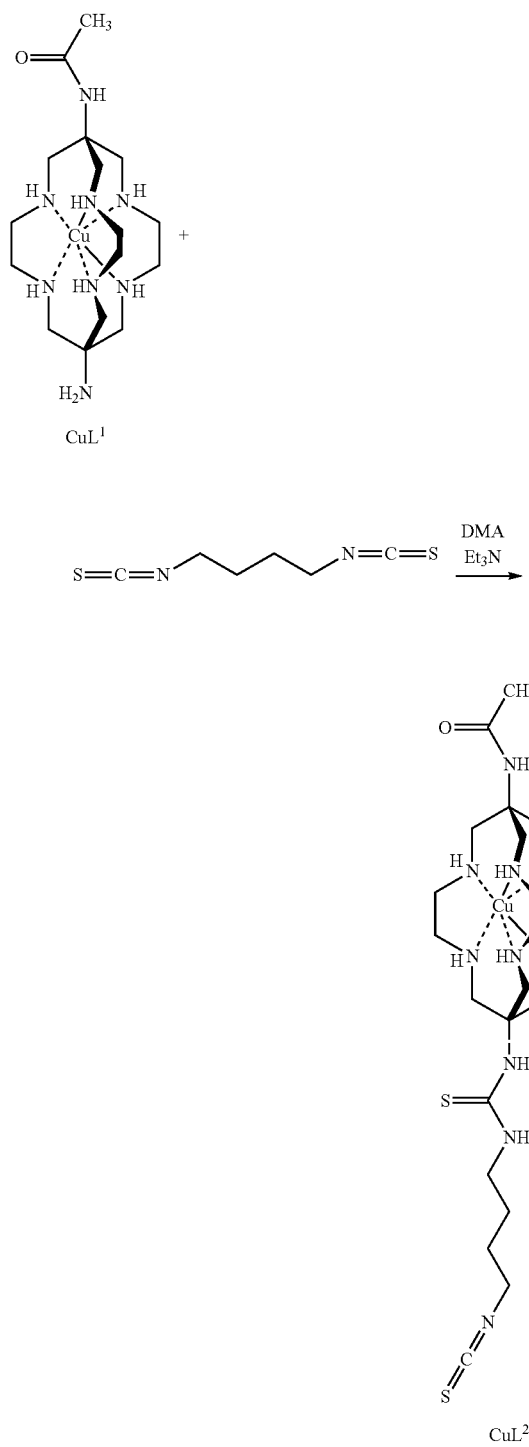

To a solution of 1,4-butanediisothiocyanate (0.195 g) in dry dimethylacetamide (3 mL) was added 5 drops of triethylamine and the mixture was heated to 60° C. To the solution was added CuL¹(ClO₄)₂(0.07 g) portion wise over 3 h before the blue solution was left to stir for 18 h. The solution was allowed to cool to room temperature before it was diluted with water and filtered through filter paper to remove excess 1,4-butanediisothiocyanate. MS: $[CuC_{22}H_{44}N_{10}OS_2]^{2+}$ m/z=295.62 (experimental), 295.62 (calculated).

Example 2 MgL³

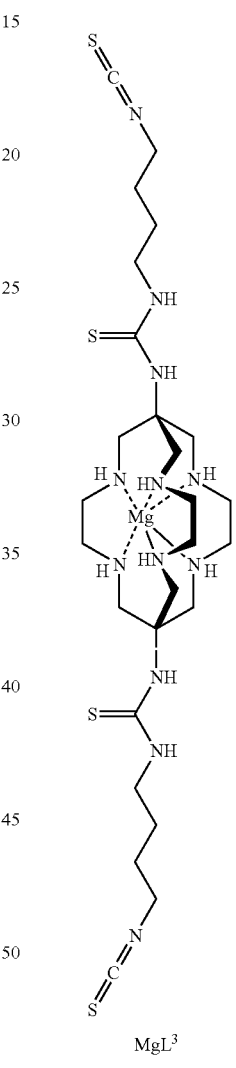

To a solution of 1,4-butanediisothiocyanate (0.144 g) in dry dimethylacetamide (1 mL) was added 5 drops of triethylamine and the mixture was heated to 60° C. To the solution was added [Mg(NH₂)₂sar](CF₃SO₃)₂ (0.05 g) portion wise over 8 h before the colourless solution was left to stir overnight. The solution was allowed to cool to room temperature before it was diluted with water and filtered through filter paper to remove excess 1,4-butanediisothiocyanate. MS: $[MgC_{26}H_{50}N_{12}S_4]^{2+}$ m/z=341.15 (experimental), 341.15 (calculated).

Example 3 CuL[4]

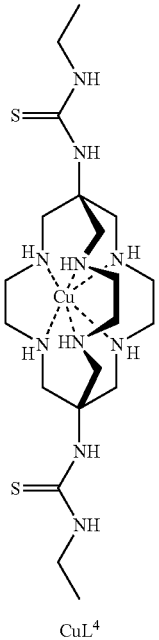

CuL[4]

To a solution of ethyl isothiocyanate (0.07 g) in dry dimethylacetamide (1 mL) was added 5 drops of triethylamine and the mixture was heated to 60° C. To the solution was added [Cu(NH$_2$)$_2$sar](ClO$_4$)$_4$ (0.11 g) and the blue solution was left to stir overnight. The solution was allowed to cool to room temperature. MS: [CuC$_{20}$H$_{44}$N$_{10}$S$_2$]$^{2+}$ m/z=275.62 (experimental), 275.62 (calculated).

Example 4 MgL[5]

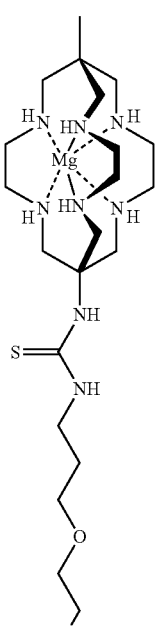

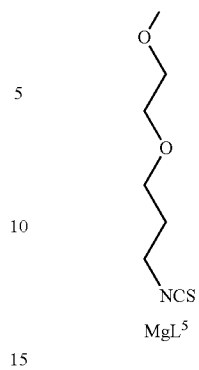

MgL[5]

To a solution of 1-isothiocyanato-3-(2-(2-(3-iosthiocyanato-propoxy) ethoxy)ethoxy)propane (0.32 g, 1.05 mmol) and triethylamine (2 equiv.) in DMA (1 mL) at 60° C. was added [Mg(NH$_2$)(CH$_3$)sar](CF$_3$SO$_3$)$_2$ (0.10 g, 0.16 mmol) in portions over 2.5 h. The reaction was allowed to cool to room temp before diethyl ether (50 mL) was added to precipitate the product. The suspension was centrifuged and the ether layer was removed and the washing process repeated. The white solid was collected by filtration, washed with diethyl ether and dried (0.11 g).). $^1$H NMR (d$_6$-DMSO): δ=0.65, s, CH$_3$; 1.74, m, 2H, CH$_2$; 1.90, m, 2H, CH$_2$; 2.4-2.6, m, 8H, CH$_2$; 2.9-3.2, m, 16H, CH$_2$, 3.4-3.7, m, 16H, CH$_2$; 6.05, br, 1H, NH; 6.71, br, 1H, NH. MS: [MgC$_{27}$H$_{55}$N$_9$O$_3$S$_2$]$^{2+}$ m/z=320.67 (experimental), 320.67 (calculated).

Example 5

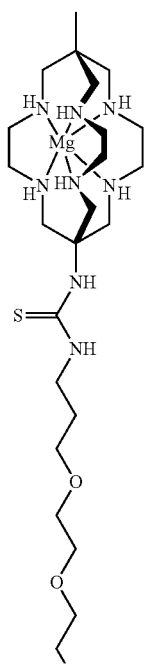

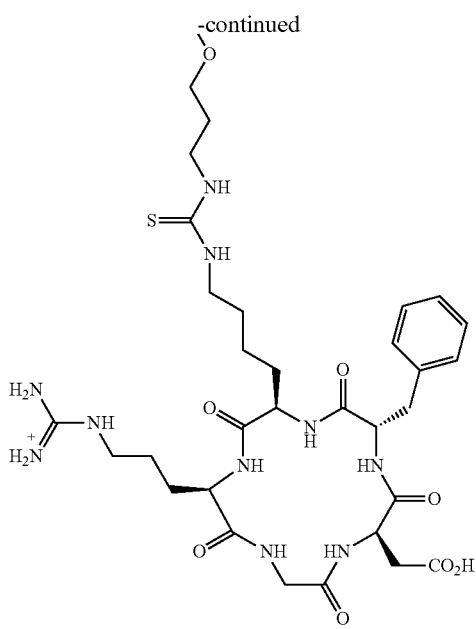

MgL⁵-cRGDfK

MgL⁵-cRGDfK

To a solution of cRGDfK (7.4 mg, 0.012 mmol) in DMSO (0.5 mL) was added [MgL⁵](CF₃SO₃)₂ (12.2 mg, 0.013 mmol) and DIPEA (6.8 uL, 0.039 mmol). The solution was left stirring for 48 h at room temperature. To the reaction was added diethyl ether to precipitate the peptide. Following centrifugation (3 min, 3600 rpm) the ether layer was decanted and the peptide was dissolved in 50% CH₃CN/H₂O and lyophilized. The crude peptide material was filtered and purified by semi-preparative reverse phase HPLC using a linear 1% A to B/min gradient (5 mL/min), where A=NH₄OAc (25 mM, pH 6.5) and B=75% CH₃CN/25% H₂O (25 mM). Fractions containing MgL⁵-cRGDfK were lyophilized. ESIMS: (+ve ion) [M +H⁺]³⁺ m/z 100% 415.26 (experimental), 415.23 (calcd).

Example 6

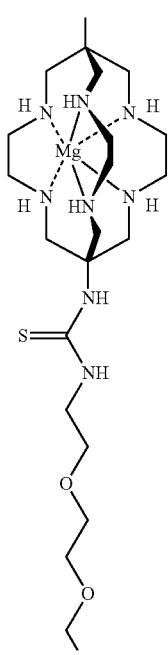

MgL⁶

MgL⁶

To a solution of 11-azido-3,6,9-trioxaundecan-1-isothiocyanate (0.07 g, 0.26 mmol) and triethylamine (40 μL, 0.26 mmol) in DMA (1 mL) at 60° C. was added [Mg(NH₂)(CH₃)sar](CF₃SO₃)₂ (0.11 g, 0.17 mmol) in portions over 1.5 h. The reaction was allowed to cool to room temp before diethyl ether (50 mL) was added to precipitate the product. The suspension was centrifuged and the ether layer was removed and the washing process repeated. The white solid was collected by filtration, washed with diethyl ether and dried (0.11 g). MS: [MgC₂₄H₅₁N₁₁O₃S]²⁺ m/z=298.72 (experimental), 298.69 (calculated).

Example 7

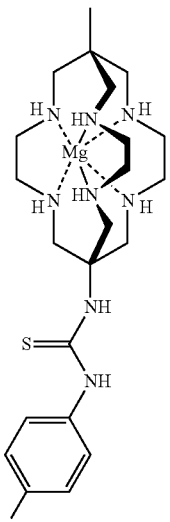

MgL⁷

MgL⁷

To a solution of 1,4-phenyldiisothiocyanate (0.06 g, 0.33 mmol) and triethylamine (14 μL, 0.1 mmol) in DMA (1 mL) at 60° C. was added [Mg(NH₂)(CH₃)sar](CF₃SO₃)₂ (0.03 g, 0.05 mmol) in portions over 1.5 h. The reaction was allowed to cool to room temp before diethyl ether (50 mL) was added to precipitate the product. The suspension was centrifuged and the ether layer was removed and the washing process repeated. The white solid was collected by filtration, washed with diethyl ether and dried. MS: [MgC₂₃H₃₉N₉S₂]²⁺ m/z=264.63 (experimental), 264.63 (calculated).

Finally, it will be appreciated that various modifications and variations of the methods and compositions of the invention described herein will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are apparent to those skilled in the art are intended to be within the scope of the present invention.

What is claimed is:

1. A method of attaching a moiety capable of binding to a biological entity to an amino substituted metal chelating ligand or a metal complex thereof the method comprising:
   (a) reacting an amino substituted metal chelating ligand or a metal complex thereof with a molecule of the formula (1):

wherein L is a bond or a linking moiety and R is H or a moiety capable of binding to a biological entity or a protected form thereof or a synthon thereof;
   (b) isolating the compound or a metal complex thereof thus produced wherein the amino substituted metal chelating ligand has the formula:

Lig-NH$_2$ wherein Lig is a nitrogen containing macrocyclic metal ligand of the formula:

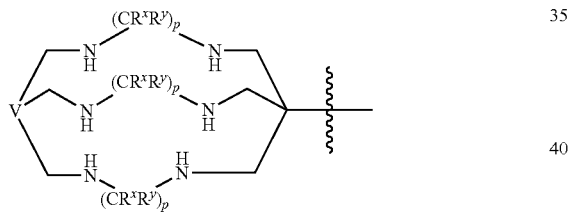

V is selected from the group consisting of N and CR$^1$;
each R$^x$ and R$^y$ are independently selected from the group consisting of H, CH$_3$, CO$_2$H, NO$_2$, CH$_2$OH, H$_2$PO$_4$, HSO$_3$, CN, CONH$_2$ and CHO;
each p is independently an integer selected from the group consisting of 2, 3, and 4;
R$^1$ is selected from the group consisting of H, OH, halogen, NO$_2$, NH$_2$, optionally substituted C$_1$-C$_{12}$alkyl, optionally substituted C$_6$-C$_{18}$aryl, cyano, CO$_2$R$^2$, NHR$^3$, N(R$^3$)$_2$;
R$^2$ is selected from the group consisting of H, halogen, an oxygen protecting group, optionally substituted C$_1$-C$_{12}$alkyl, optionally substituted C$_2$-C$_{12}$ alkenyl, optionally substituted C$_2$-C$_{12}$alkynyl and optionally substituted C$_2$-C$_{12}$heteroalkyl;
each R$^3$ is independently selected from the group consisting of H, a nitrogen protecting group, optionally substituted C$_1$-C$_{12}$alkyl, —(C═O)-substituted C$_1$-C$_{12}$alkyl, optionally substituted C$_2$-C$_{12}$alkenyl, optionally substituted C$_2$-C$_{12}$alkynyl and optionally substituted C$_2$-C$_{12}$heteroalkyl.

2. A method according to claim 1, wherein Lig is selected from the group consisting of:

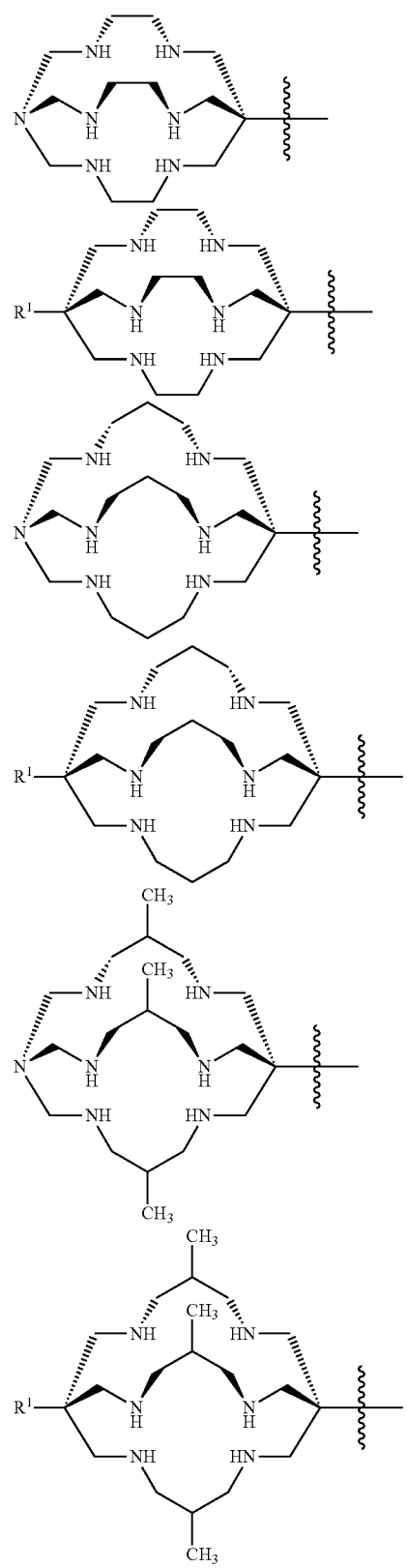

wherein R$^1$ is as defined in claim 1.

3. A method according to claim 1, wherein L is a group of the formula

—(CH$_2$)$_a$—, wherein optionally one or more of the CH$_2$ groups may be independently replaced by a heteroatomic group selected from S, O, P and NR$^4$ where R$^4$ is selected from the group consisting of H, optionally substituted C$_1$-C$_{12}$alkyl, optionally substituted C$_3$-C$_{12}$cycloalkyl, optionally substituted C$_6$-C$_{18}$aryl, and optionally substituted C$_1$-C$_{18}$heteroaryl;

a is an integer selected from the group consisting of 1, 2, 3, 4, 5, 6, 7, 8, 9, 10, 11, 12, 13, 14 and 15.

4. A method according to claim 3 wherein L is selected from the group consisting of —CH$_2$—, —CH$_2$CH$_2$—, —CH$_2$CH$_2$CH$_2$—, —CH$_2$CH$_2$CH$_2$CH$_2$- and —CH$_2$OCH$_2$—.

5. A method according to claim 1, wherein L is —CH$_2$CH$_2$CH$_2$CH$_2$—.

6. A method according to claim 1, wherein R is a moiety capable of taking part in a click chemistry reaction with a complementary moiety on a biological entity.

7. A method according to claim 1, wherein R is selected from the group consisting of —NCS, CO$_2$H, NH$_2$, an azide, an alkyne, an isonitrile, a tetrazine, or a protected form thereof or a synthon thereof.

8. A method according to claim 1, wherein during reaction with a compound of formula (1) the amino substituted metal chelating ligand is in the form of its metal complex.

9. A method according to claim 8 wherein the metal is magnesium.

10. A compound of the formula:

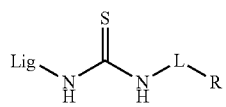

(1)

L is a bond or a linking moiety;
R is H or a moiety capable of binding to a biological entity or a protected form thereof or a synthon thereof;
wherein Lig is a nitrogen containing cage metal ligand of the formula:

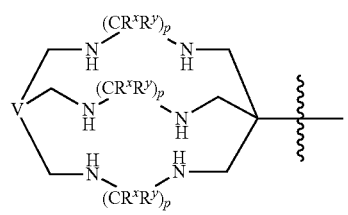

V is selected from the group consisting of N and CR$^1$;
each R$^x$ and R$^y$ are independently selected from the group consisting of H, CH$_3$, CO$_2$H, NO$_2$, CH$_2$OH, H$_2$PO$_4$, HSO$_3$, CN, CONH$_2$ and CHO;
each p is independently an integer selected from the group consisting of 2, 3, and 4;
R$^1$ is selected from the group consisting of H, OH, halogen, NO$_2$, NH$_2$, optionally substituted C$_1$-C$_{12}$alkyl, optionally substituted C$_6$-C$_{18}$aryl, cyano, CO$^2$R$^2$, NHR$^3$, N(R$^3$)$_2$;
R$^2$ is selected from the group consisting of H, halogen, an oxygen protecting group, optionally substituted C$_1$-C$_{12}$alkyl, optionally substituted C$_2$-C$_{12}$alkenyl, optionally substituted C$_2$-C$_{12}$alkynyl and optionally substituted C$_2$-C$_{12}$heteroalkyl;
each R$^3$ is independently selected from the group consisting of H, a nitrogen protecting group, optionally substituted C$_1$-C$_{12}$alkyl, —(C=O)-substituted C$_1$-C$_{12}$alkyl, optionally substituted C$_2$-C$_{12}$alkenyl, optionally substituted C$_2$-C$_{12}$alkynyl and optionally substituted C$_2$-C$_{12}$ heteroalkyl.

11. A compound according to claim 10 wherein Lig is selected from the group consisting of:

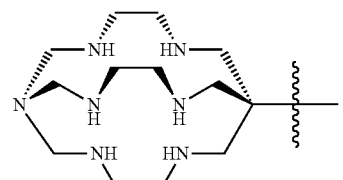

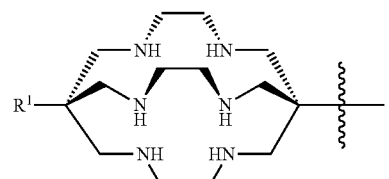

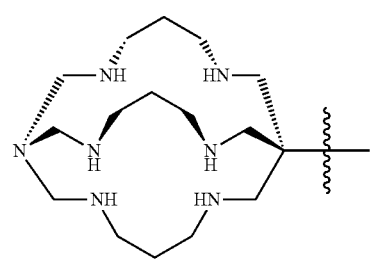

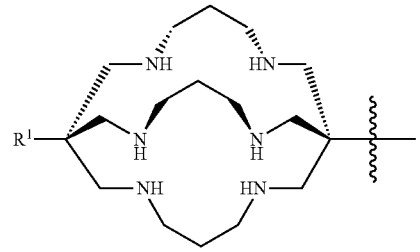

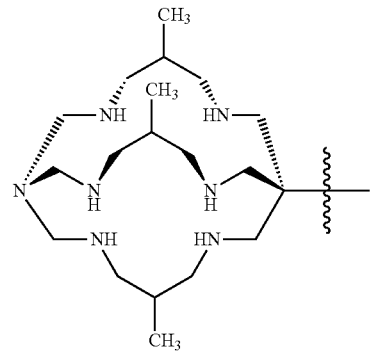

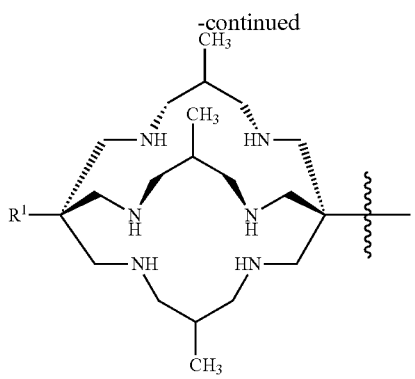

wherein is as defined in claim 10.

12. A compound according to claim 10, wherein L is a group of the formula —(CH$_2$)$_a$—, wherein optionally one or more of the CH$_2$ groups may be independently replaced by a heteroatomic group selected from S, O, P and NR$^4$ where R$^4$ is selected from the group consisting of H, optionally substituted C$_1$-C$_{12}$alkyl, optionally substituted C$_3$-C$_{12}$cycloalkyl, optionally substituted C$_6$-C$_{18}$aryl, and optionally substituted C$_1$-C$_{18}$heteroaryl;

a is an integer selected from the group consisting of 1, 2, 3, 4, 5, 6, 7, 8, 9, 10, 11, 12, 13, 14 and 15.

13. A compound according to claim 10, wherein L is selected from the group consisting of —CH$_2$—, —CH$_2$CH$_2$—, —CH$_2$CH$_2$CH$_2$—, —CH$_2$CH$_2$CH$_2$CH$_2$— and —CH$_2$OCH$_2$—.

14. A compound according to claim 10, wherein L is —CH$_2$CH$_2$CH$_2$—.

15. A compound according to claim 10, wherein R is a moiety capable of taking part in a click chemistry reaction with a complementary moiety on a biological entity.

16. A compound according to claim 10, wherein R is selected from the group consisting of —NCS, CO$_2$H, NH$_2$, an azide, an alkyne, an isonitrile, a tetrazine, or a protected form thereof or a synthon thereof.

17. A compound according to claim 10 selected from the group consisting of:

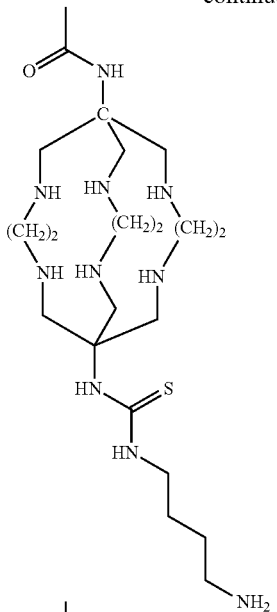

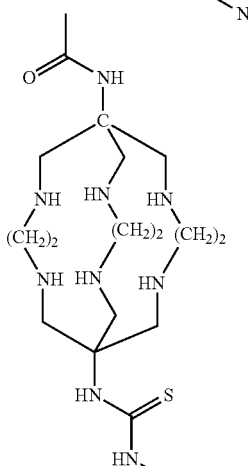

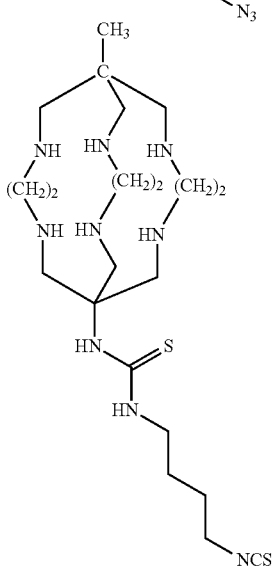

53
-continued
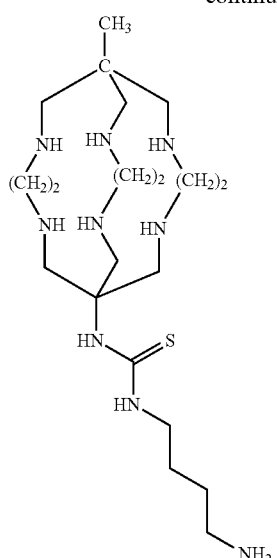
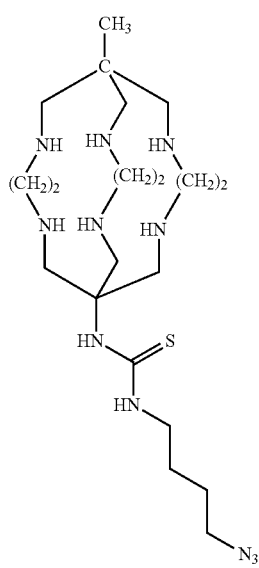
54
-continued
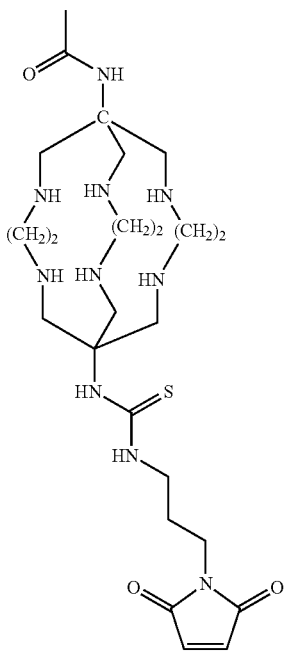
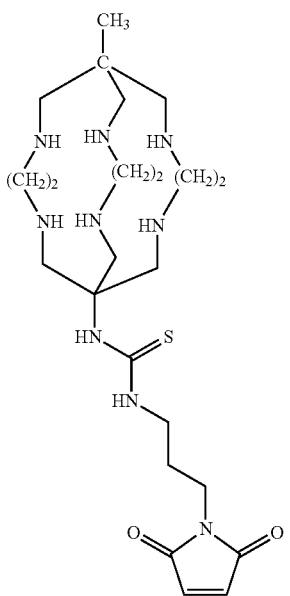

55
-continued
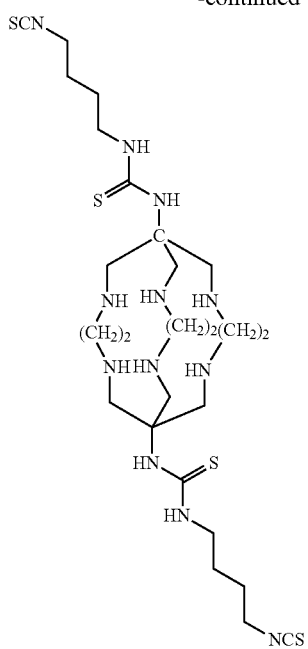
56
-continued
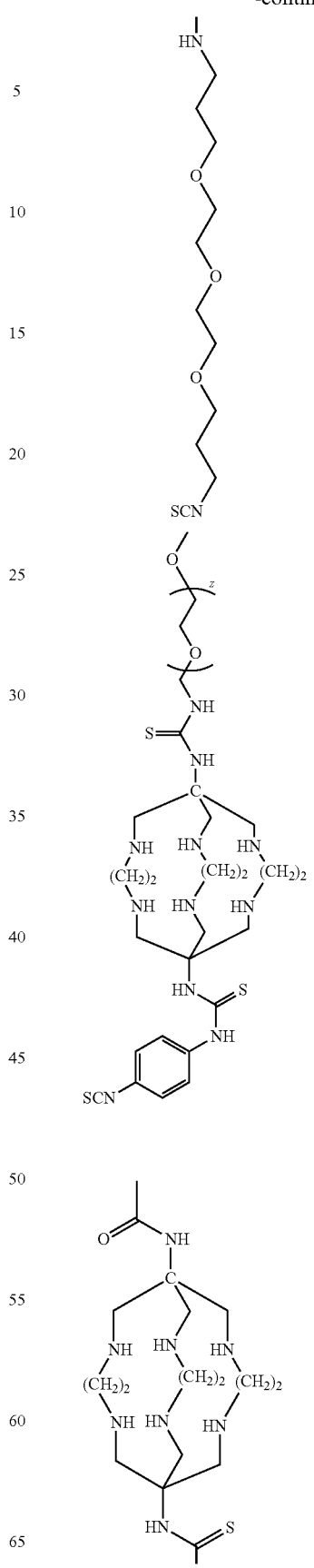

57
-continued
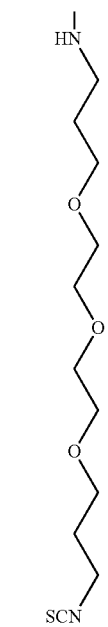
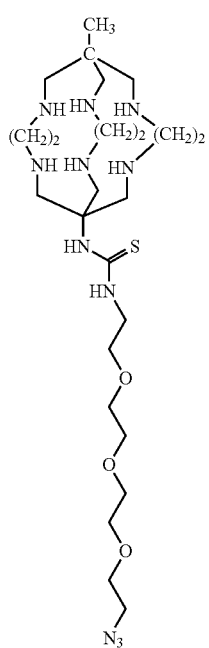
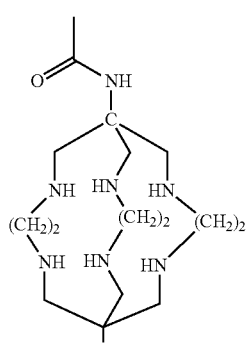
58
-continued
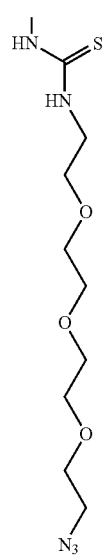
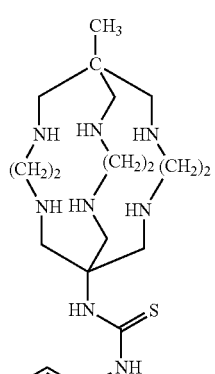
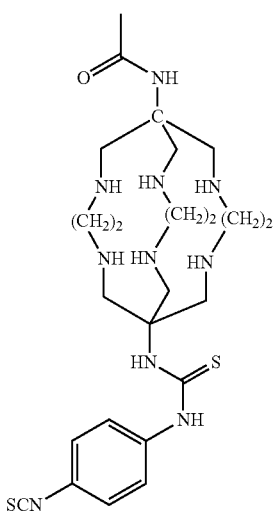

59
-continued
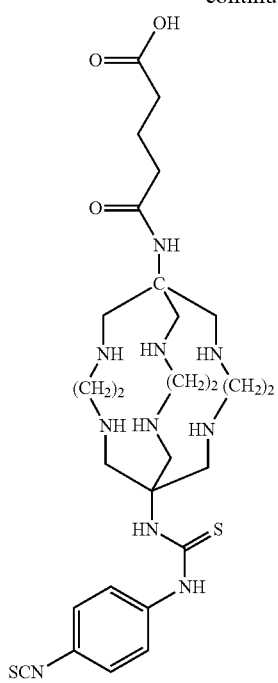
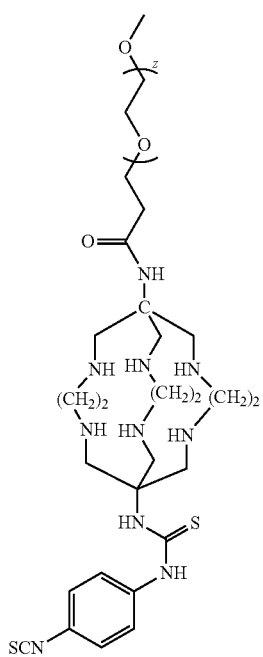
60
-continued
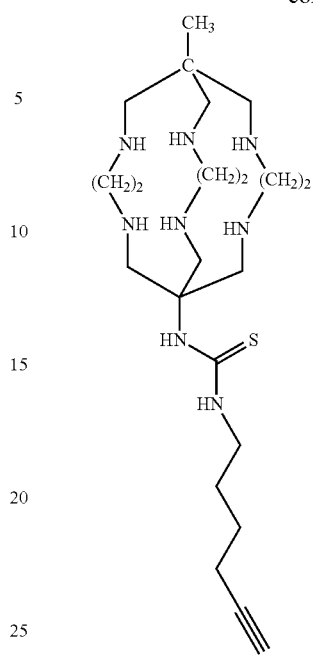
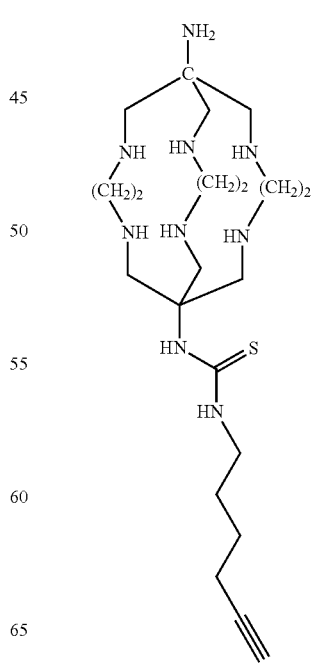

61
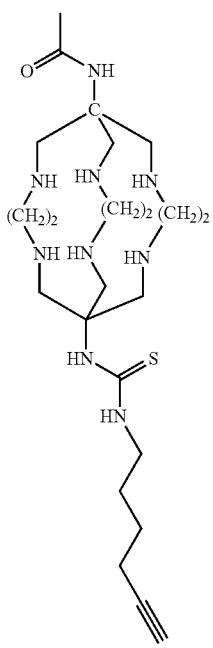
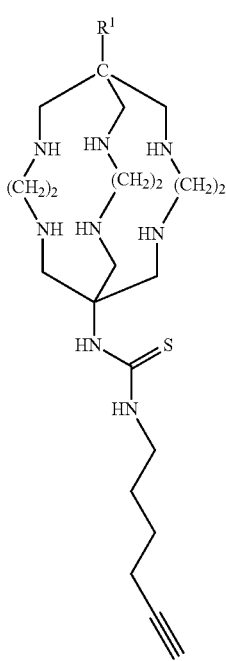
62
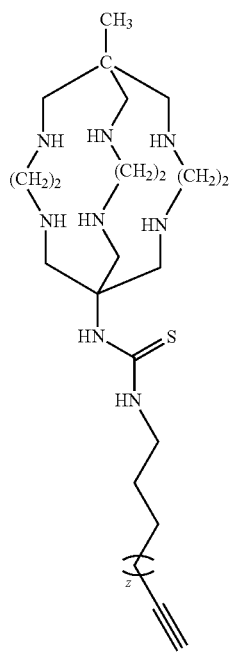
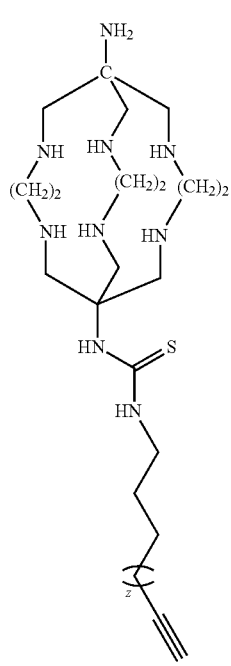

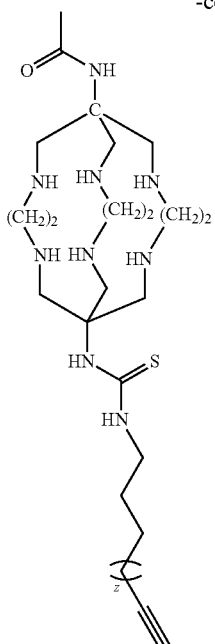
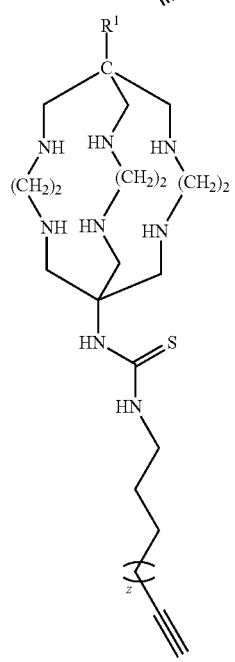
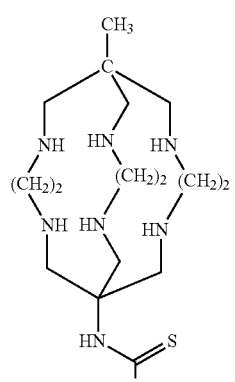
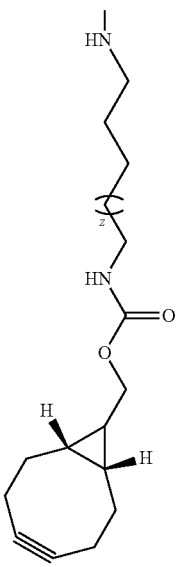
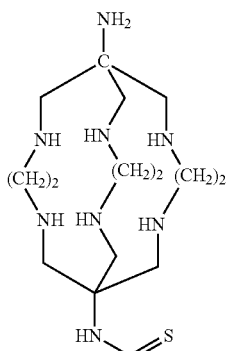
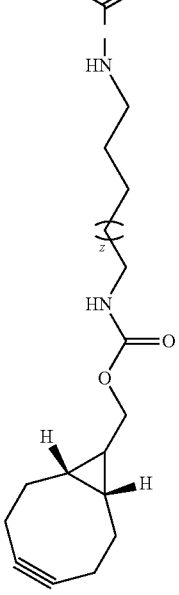

65
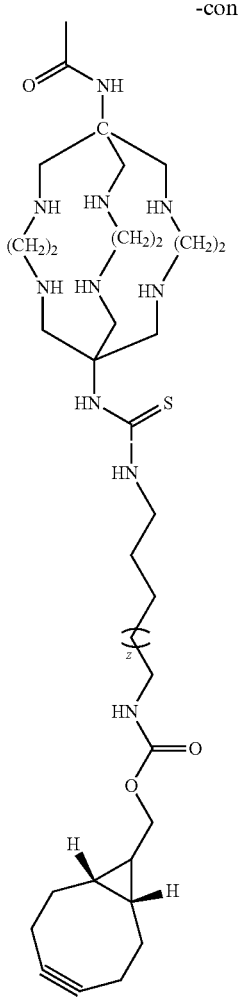
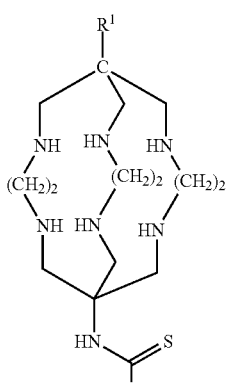
66
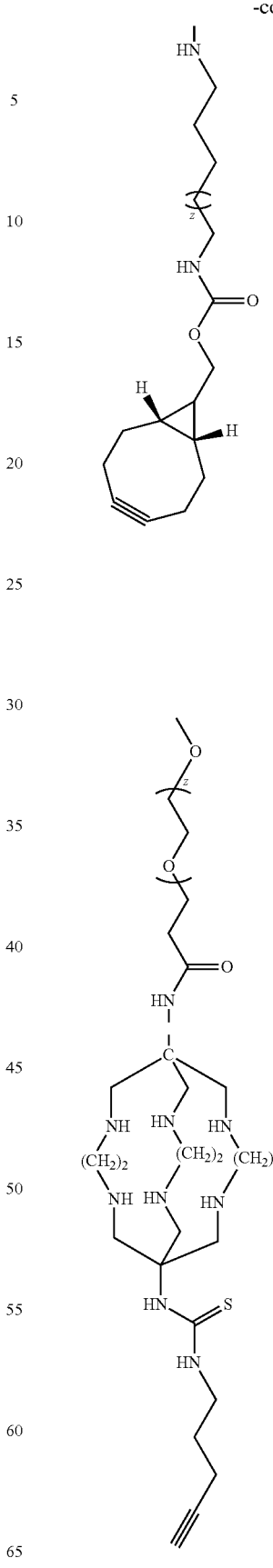

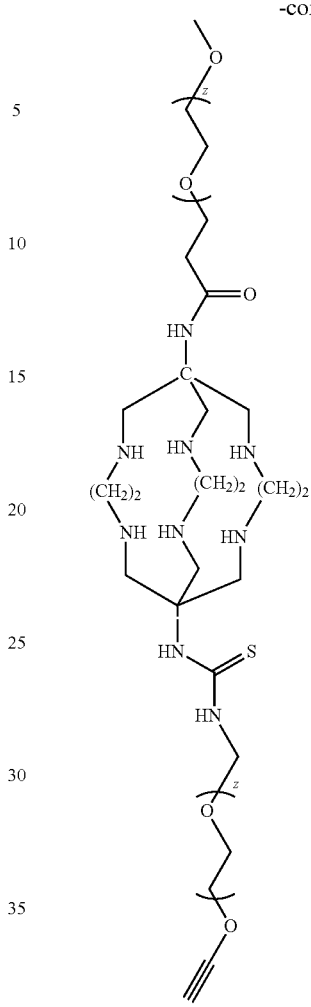

z is an integer from 0 to 12 or a metal complex thereof.

18. A compound according to claim 10, wherein the nitrogen containing macrocyclic metal ligand is coordinated with a metal ion.

19. A compound according to claim 18 wherein the metal in the metal ion is selected from the group consisting of Cu, Tc, Gd, Ga, In, Co, Re, Fe, Au, Mg, Ca, Ag, Rh, Pt, Bi, Cr, W, Ni, V, Ir, Pt, Zn, Cd, Mn, Ru, Pd, Hg, and Ti.

20. A compound according to claim 18 wherein the metal in the metal ion is a radionuclide selected from the group consisting of Cu, Tc, Gd, Ga, In, Co, Re, Fe, Au, Ag, Rh, Pt, Bi, Cr, W, Ni, V, Ir, Pt, Zn, Cd, Mn, Ru, Pd, Hg, and Ti.

21. A compound according to claim 18, wherein the metal in the metal ion is a radionuclide selected from the group consisting of $^{60}$Cu, $^{62}$Cu, $^{64}$Cu and 67Cu.

* * * * *